US011324914B2

(12) United States Patent
Baillie et al.

(10) Patent No.: US 11,324,914 B2
(45) Date of Patent: May 10, 2022

(54) PERCUSSIVE VENTILATION BREATHING HEAD AND ACCESSORIES

(71) Applicant: Percussionaire Corporation, Sandpoint, ID (US)

(72) Inventors: Mark Baillie, Dover, ID (US); Shawn Goughnour, Bonners Ferry, ID (US); Giles Wilson, Livermore, CA (US)

(*) Notice: Subject to any disclaimer, the term of this patent is extended or adjusted under 35 U.S.C. 154(b) by 336 days.

(21) Appl. No.: 16/391,481

(22) Filed: Apr. 23, 2019

(65) Prior Publication Data

US 2020/0139076 A1 May 7, 2020

Related U.S. Application Data

(60) Provisional application No. 62/754,340, filed on Nov. 1, 2018.

(51) Int. Cl.
| | |
|---|---|
| *A61M 16/20* | (2006.01) |
| *A61M 16/00* | (2006.01) |
| *A61M 16/10* | (2006.01) |

(52) U.S. Cl.
CPC ........ *A61M 16/20* (2013.01); *A61M 16/0012* (2014.02); *A61M 16/0096* (2013.01); *A61M 16/022* (2017.08); *A61M 16/105* (2013.01)

(58) Field of Classification Search
CPC .............. A61M 16/20; A61M 16/0012; A61M 16/022; A61M 16/0096; A61M 16/105;
(Continued)

(56) References Cited

U.S. PATENT DOCUMENTS

| | | | | |
|---|---|---|---|---|
| 3,171,597 A | * | 3/1965 | Baier | F24D 3/08 237/19 |
| 5,165,398 A | | 11/1992 | Bird | |

(Continued)

FOREIGN PATENT DOCUMENTS

| | | | | |
|---|---|---|---|---|
| CN | 207886310 U | * | 9/2018 | |
| GB | 2052270 A | * | 1/1981 | .......... A61M 16/009 |

(Continued)

OTHER PUBLICATIONS

Y. Shehabi and et al, "Tests of Six Continuous Flow CPAP Devices", Anaesthesia and Intensive Care, vol. 19, No. 2, May 1991 (Year: 1991).*

(Continued)

*Primary Examiner* — Douglas Kay
(74) *Attorney, Agent, or Firm* — Robert C. Kain; Scott D. Smiley; Scott M. Garrett

(57) ABSTRACT

A percussive ventilation breathing head is adapted to be supplied with a flow of pulsatile gas fed to an elongated breathing head body at a proximal end thereof. The breathing head body defines an interior passageway therein. A reciprocating injector shuttle is movably mounted in the breathing head passageway. The shuttle moves distally due to the pulsatile gas, assisted by a diaphragm and a venturi-like jet nozzle which nozzle pulls nebulized aerosol from a depending plenum and a nebulizer attached below the depending plenum. A depending body defines the plenum. The generally cylindrical nebulizer is attached below the depending body. The shuttle is also biased in a proximal direction within the interior passageway and moves proximally due to the bias. The shuttle defines an internal flow passage from a proximal shuttle input port to a distal shuttle output port at the distalmost mouth of the percussive ventilation breathing head body.

13 Claims, 21 Drawing Sheets

(58) Field of Classification Search
CPC .... A61M 2205/582; A61M 2205/7536; A61M 2016/0027; A61M 16/208; A61M 16/209; A61M 16/127; A61M 16/06; A61M 16/0006; A61M 16/0858; A61M 16/0816

See application file for complete search history.

(56) References Cited

U.S. PATENT DOCUMENTS

| | | | |
|---|---|---|---|
| 5,862,802 A | 1/1999 | Bird | |
| 6,581,600 B2 | 6/2003 | Bird | |
| 6,595,203 B1 * | 7/2003 | Bird | A61M 11/06 128/200.14 |
| 8,347,883 B2 | 1/2013 | Bird | |
| 2007/0277828 A1 * | 12/2007 | Ho | A61M 16/08 128/206.21 |
| 2009/0126734 A1 * | 5/2009 | Dunsmore | A61M 16/0858 128/203.25 |
| 2012/0259180 A1 * | 10/2012 | Rock | B62J 9/22 600/300 |

FOREIGN PATENT DOCUMENTS

| | | | | |
|---|---|---|---|---|
| WO | WO 02/43643 A2 | 6/2002 | | |
| WO | WO 2016/057847 A1 | 4/2016 | | |
| WO | WO-2017162421 A1 * | 9/2017 | ........... | F16K 24/044 |

OTHER PUBLICATIONS

M. P. Garcia, "Ambient Air Cooling of Electronics in an Outdoor Environment", INTELEC 2004. 26th Annual International Telecommunications Energy Conference, Sep. 19-23, 2004 (Year: 2004).*

Extended European search report for Application No. 19206335.2; Date Completion Mar. 12, 2020.

Millipore, "Filter Integrity Test Methods" Integritest and Durapore are registered trademarks ofMillipore Corp. or an affiliated company. Lit. No. TB039, Printed in USA May 1999.

Millipore Sigma, http://www.emdmillipore.com/US/en/life-science-research/chromatography-sample-preparation/membrane-learning-center/Flow-Rate/ZMSb.qB.thOAA . . . .

* cited by examiner

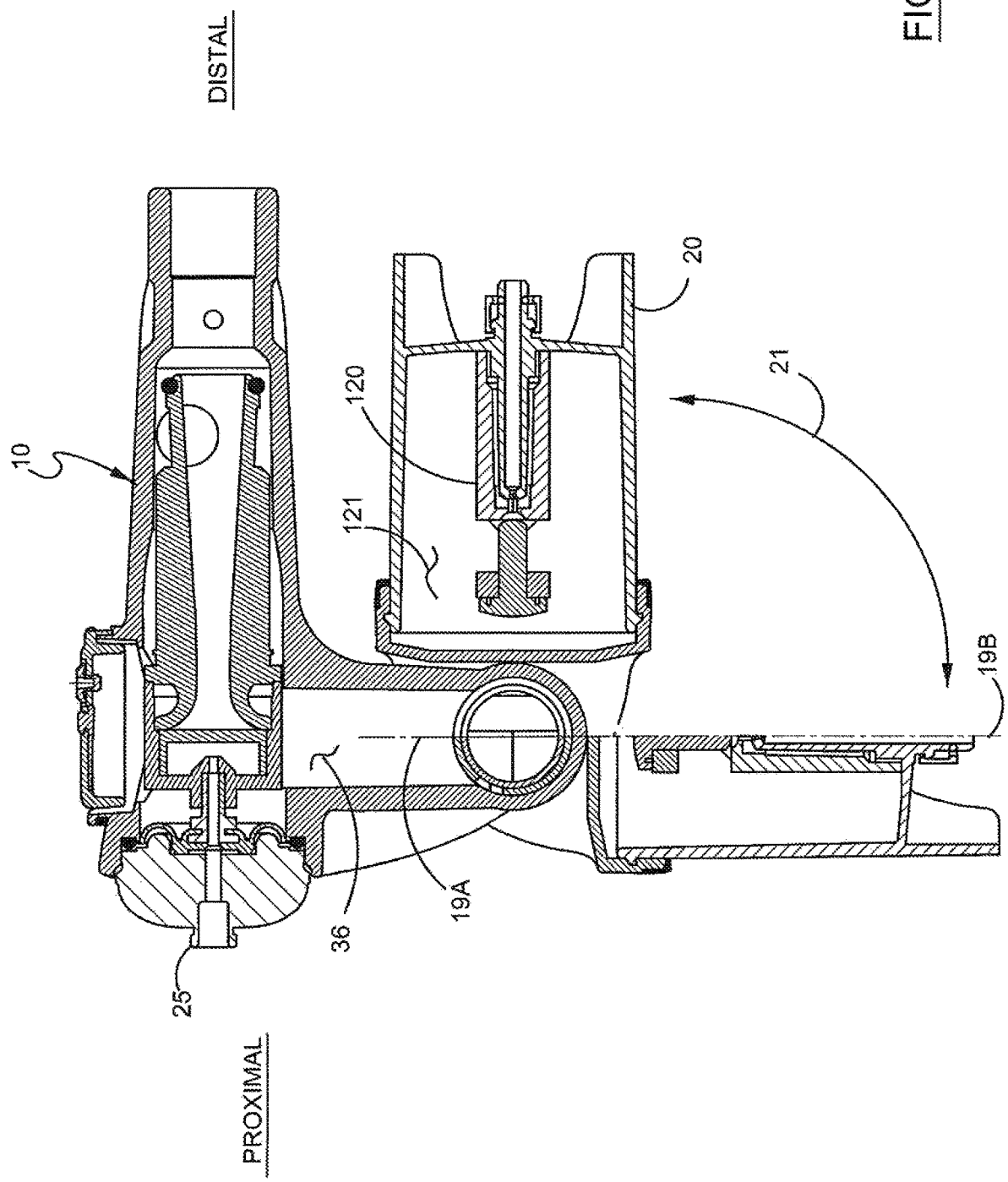

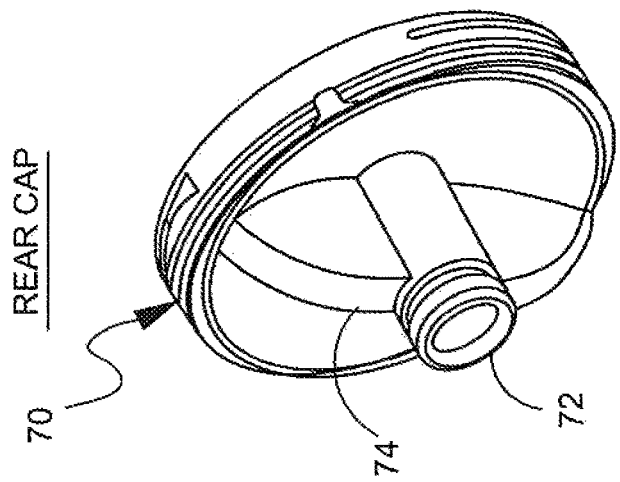
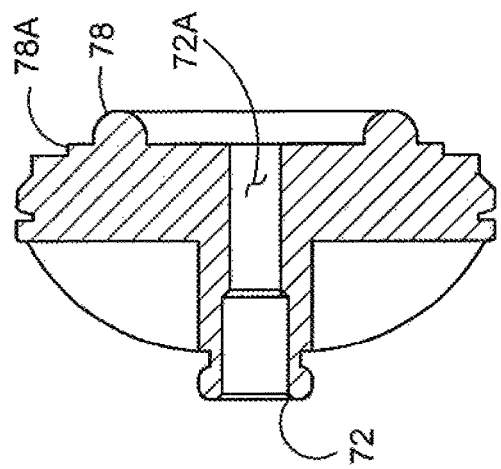
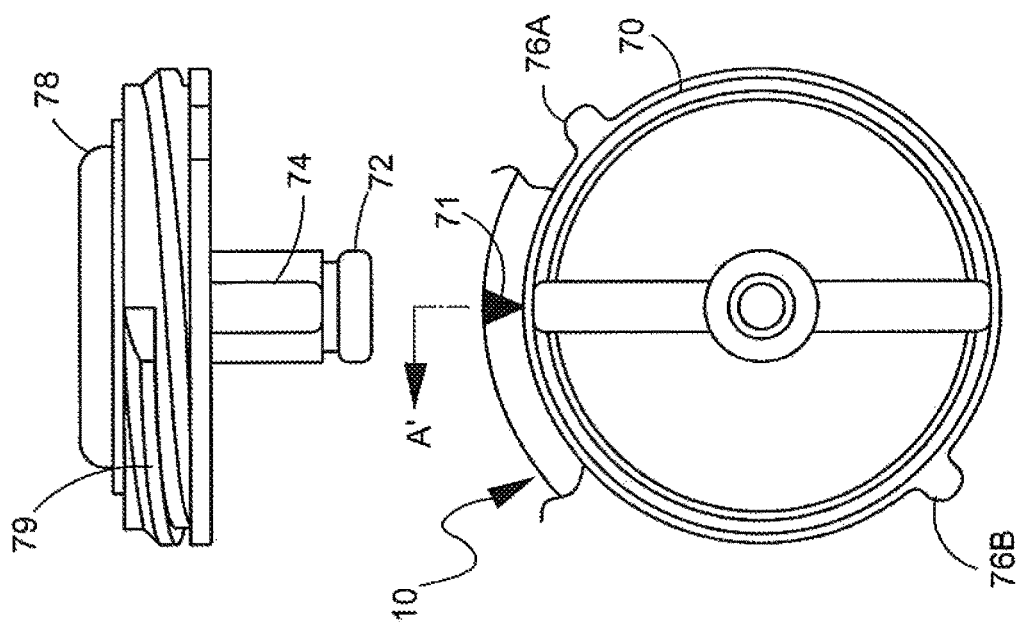

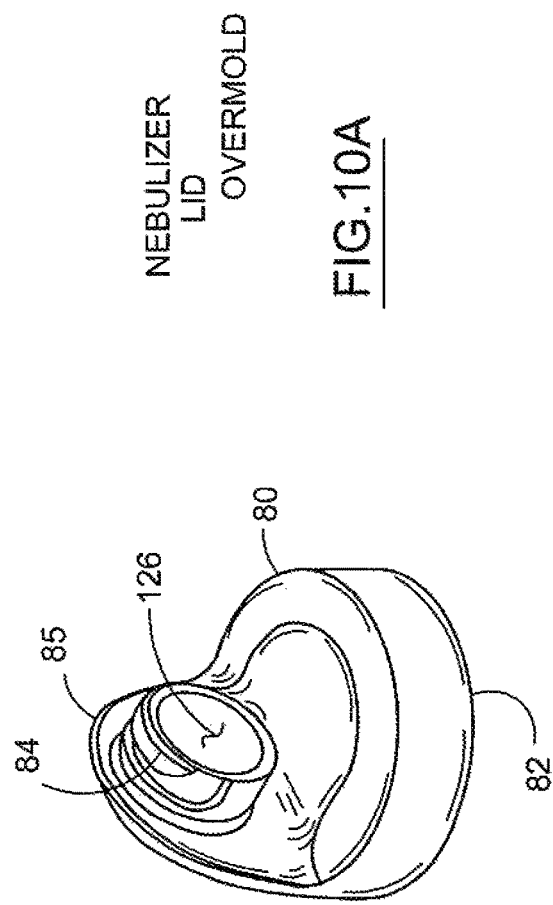
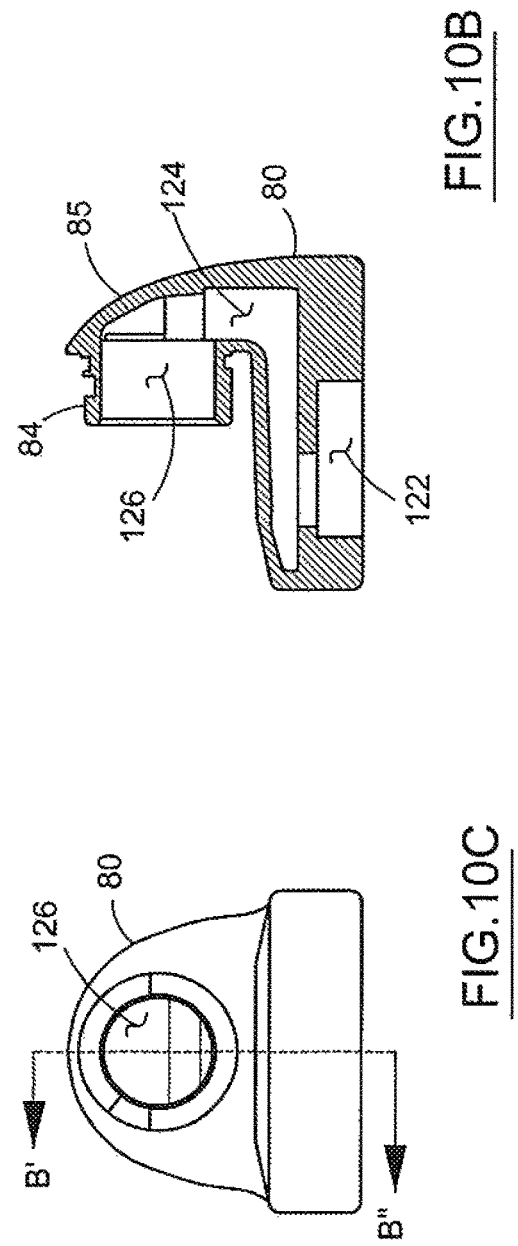
NEBULIZER LID OVERMOLD
FIG.10A
FIG.10B
FIG.10C

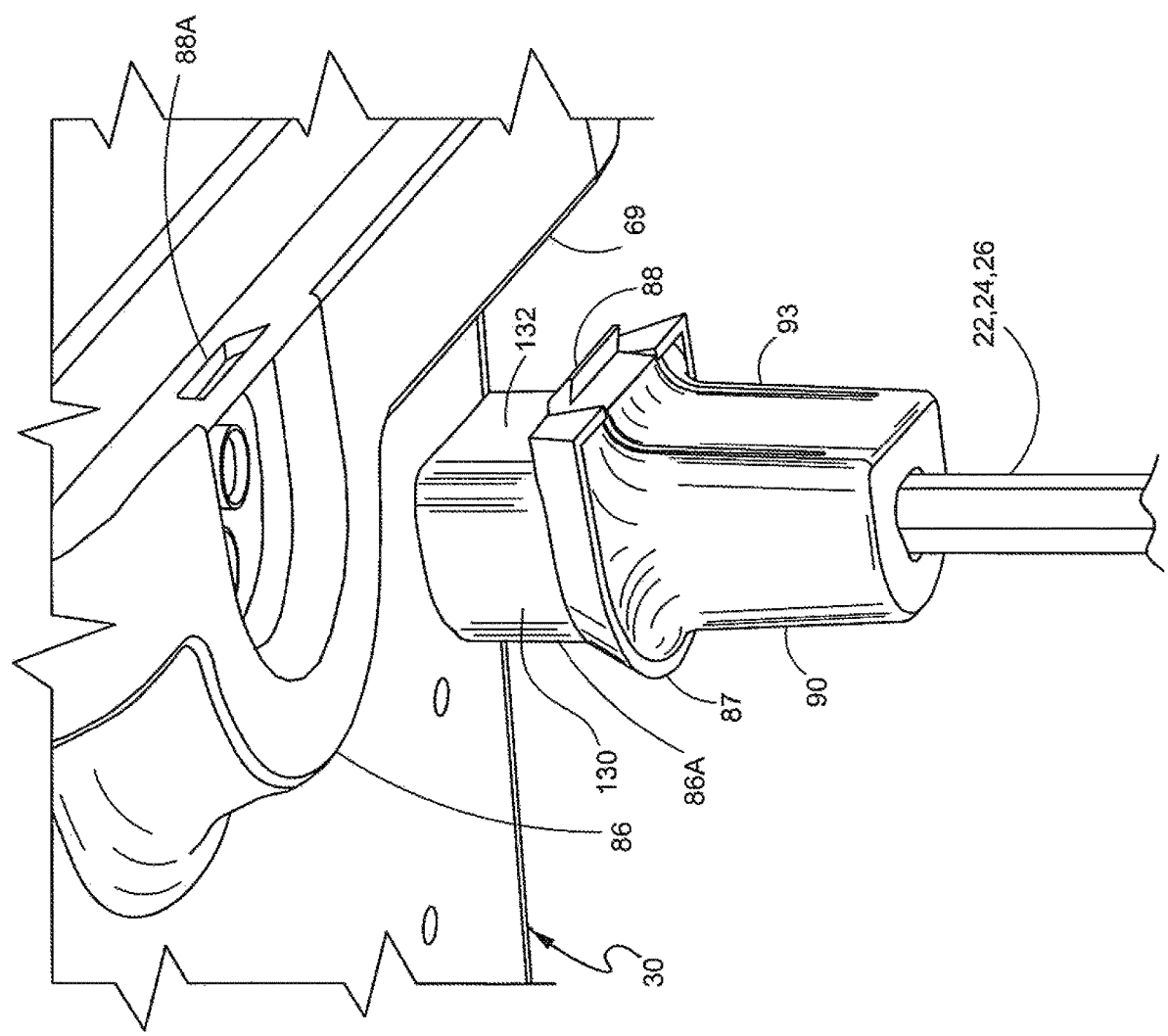

PERCUSSIVE VENTILATION BREATHING HEAD AND ACCESSORIES

This is a regular patent application based upon and claiming the priority of provisional patent application Ser. No. 62/754,340, filed Nov. 1, 2018, the contents of which is incorporated herein by reference thereto.

The percussive ventilation breathing head administers intermittent percussive ventilation to a patient's airway. In general, the breathing head includes a nebulizer depending from the generally cylindrical headpiece via a depending body. The breathing head is supplied with a constant pressurized gas which nebulizes liquid contained in the nebulizer unit. Aerosol from the nebulizer passes through a plenum in the depending body to a proximally disposed venturi-like passageway in the breathing head and into a mouthpiece at a distal end of the breathing head and further into the airway of the patient to begin inflation of the patient's lungs during commencement of the inspiratory phase. The inventive breathing head includes several improvements, each unique in their use, construction and implementation, including a unitary entrainment valve (such as a flapper valve, a one-way over-pressure valve, a hydrophobic filter, or overpressure valve); a transparent viewport channel alongside said elongated breathing head body; a breathing head having an operational configuration mode and a disassembled cleaning mode; a unique sealable attachment between the nebulizer body and an overmold lid on a depending body defining a plenum; and first and second complementary connective surfaces on the conjoined terminal ends of the pulsatile gas/pressurized gas/pressure sensing lines and formed in the control housing such that said first and second connective surfaces only interface in a single positional manner.

BACKGROUND OF THE INVENTION

Nebulizers are well known. One configuration of a percussive ventilation breathing head is described in U.S. Pat. No. 6,595,203 to Bird, the contents of which is incorporated herein by reference thereto.

OBJECTS OF THE INVENTION

It is an object of the present invention to provide an improved percussive ventilation breathing head.

It is another object of the present invention to provide the breathing head with a unitary entrainment valve either as a flapper valve, a one-way over-pressure valve, a hydrophobic filter, or overpressure valve.

It is a further object of the present invention to provide an improved percussive ventilation breathing head with a transparent viewport channel alongside said elongated breathing head body such that the patient or caregiver can view the absence or presence of excess fluid in the flow passages in the breathing head body (especially mucus which may accumulate in the breathing head body).

It is an additional object of the present invention to provide an improved percussive ventilation breathing head which has an operational configuration mode and a disassembled cleaning mode, such that when disassembled, the percussive ventilation breathing head can be easily cleaned and reassembled for future use.

It is another object of the present invention to provide an improved percussive ventilation breathing head with a unique sealable attachment between the nebulizer body and an overmold lid on a depending body defining a plenum, such that (a) during assembly, the seal is confirmed by audible and/or tactile responses and (b) the turn-and-click, one-way attachment is nearly foolproof, and (c) during non-use, the unique sealable attachment permits the nebulizer body to be rotated and positioned 90 degrees from the depending body centerline such that the nebulizer body is positioned below the elongated percussive ventilation breathing head and the centerline through the nebulizer body is parallel to the centerline through the elongated percussive ventilation breathing head.

It is a further object of the present invention to provide an improved percussive ventilation breathing head with first and second complementary connective surfaces, one connective surface on the conjoined terminal ends of the pulsatile gas/pressurized gas/pressure sensing lines and a second connective surface formed in the control housing such that said first and second connective surfaces only interface in a single positional manner. As a result, the interconnection is a one-way connection between (a) a control housing for the control system, which control system supplies a flow of pulsatile gas and a flow of pressurized gas to the breathing head and which control system monitors pressure in the breathing head via a pressure sensor line, and (b) the percussive ventilation breathing head system.

SUMMARY OF THE INVENTION

The percussive ventilation breathing head is adapted to be supplied with a flow of pulsatile gas fed to an elongated breathing head body at a proximal end thereof. The breathing head body defines an interior passageway therein. A reciprocating injector shuttle is movably mounted in the breathing head passageway. The shuttle moves distally due to the pulsatile gas, assisted by a diaphragm and a venturi-like jet nozzle which nozzle pulls nebulized aerosol from a depending plenum and a nebulizer attached below the depending plenum. A depending body defines the plenum between the breathing head flow passages and the nebulizer. The generally cylindrical nebulizer is attached below the depending body. The shuttle is biased in a proximal direction within the interior passageway and moves proximally due to the bias. The shuttle defines an internal flow passage from a proximal shuttle input port to a distal shuttle output port at the distalmost mouth of the percussive ventilation breathing head body.

A unitary entrainment valve on the breathing head body has an entrainment valve body defining an entrainment valve chamber in fluid communication with the proximal shuttle input port. In one embodiment, the entrainment valve includes a valve flapper biased closed and separating an ambient environment from the entrainment valve chamber. When the pressure in the internal shuttle flow passage falls below a predetermined value (set by the flapper bias), the entrainment valve opens to the ambient and ambient air is introduced and mixed with the aerosol in the proximal shuttle input port area. An over-pressure valve on the entrainment valve body adapted to release aerosol to the ambient at a predetermined pressure set by the valve. In another embodiment, a hydrophobic filter mounted in the entrainment valve body separating the ambient from the entrainment valve chamber and permitting substantially one-way ambient air flow to the entrainment valve chamber.

An interface coupler is also disclosed which is adapted to be coupled to a ventilator line between a conventional ventilator and a patient for continuing patient treatment. The interface coupler includes an interface coupler body and a coupler through channel defined between a coupler input port and a coupler output port. These interface input and output ports are to be coupled in the ventilator line. The interface coupler body has a pulsatile flow port coupler in fluid communication with the coupler channel via a one-way flow valve mounted in the pulsatile flow port coupler. Also, a supplemental air valve may be included. The supplemental air valve body is open to the coupler channel. The supplemental air valve has a variable valve control stem between a supplemental air vent open to the ambient and the coupler channel.

The percussive ventilation breathing head may also include an elongated transparent viewport channel alongside the outside of the elongated breathing head body. The view channel extends from a pressure sensor portal in the breathing head body to the proximal end of the breathing head body. The pressure sensor portal is defined in the breathing head body near the distal mouth of the breathing head. In this manner, the sensor portal can be used to sense pressure near the patient's airway. The elongated transparent viewport channel terminates in a pressure sensor fitting at the proximal end of the breathing head body. A pressure sending tube is attached to this fitting such that pressure can be sensed by a control monitor in a control housing which controller also supplies pulsatile gas to the breathing head and supplies pressurized gas to the head. The pressurized gas is fed to the nebulizer.

The elongated breathing head body also includes an end cap having, on a proximal cap region, an aerosol tube fitting adapted to receive the pulsatile gas flow thereat. The end cap has, on a distal cap region, the diaphragm mounted thereon. The diaphragm forms an expandable chamber between the diaphragm and the distal cap region. Pulsatile gas flow from the aerosol tube fitting expands the diaphragm's expandable chamber. The venturi-like jet nozzle is mounted on the diaphragm at a distal diaphragm region. The venturi-like jet nozzle is in fluid communication with the expandable chamber and the proximal shuttle input port, thereby permitting pulsatile gas flow to the proximal shuttle input port. The shuttle moves distally due to the diaphragm movement and the pulsatile gas ejected from the venturi-like jet nozzle into the proximal shuttle input port. The shuttle is biased in a proximal direction within the breathing head passageway by a biasing means and moves proximally due to the biasing means.

The percussive ventilation breathing head has (a) an operational configuration wherein upon application of the pulsatile gas and the nebulized gas flow from the depending plenum, the shuttle is adapted to move distally into the proximal shuttle passageway and then move proximally due to a biasing spring or other biasing mechanism, and (b) a disassembled cleaning mode wherein the end cap is removed from the proximal end of the elongated breathing head body and the shuttle is withdrawn from the breathing head body interior passageway, such that the end cap, elongated breathing head body, and shuttle is adapted to be cleaned. In most cases, the spring is removed. To facilitate cleaning, the unitary entrainment valve may also removably attached the breathing head body.

A generally cylindrical nebulizer body is threadably removably attached to an overmold lid at the bottom of the depending body. The overmold lid forms a lower interior lid chamber in fluid communication with the nebulizer body and forms a vertical lid chamber and a horizontal lid chamber both in fluid communication with the lower interior lid chamber and the nebulizer body. The overmold lid has a horizontal threaded lid element about a portion of the horizontal lid chamber. The depending body has a horizontal depending body threaded stem formed at a lower end region thereof with a threaded stem complementary to the horizontal threaded lid element. The horizontal depending body threaded stem sealingly engaging the horizontal threaded lid element.

Tabs act as male nebulizer threads and the overmold lid in the lower interior lid chamber forms horizontal overmold lid threads complementary to the male nebulizer threads. The horizontal overmold lid threads sealingly engage the male nebulizer threads. The overmold lid threads and the male nebulizer threads include one or more locking mode elements. For example, these locking mode elements include (I) an audible click lock indicator formed by a pair of complementary detents formed on the horizontal overmold lid threads and the male nebulizer threads; and (ii) a tactile click lock indicator formed by a pair of complementary detents formed on the horizontal overmold lid threads and the male nebulizer threads.

To connect the percussive ventilation breathing head to a control system (the control system also supplying pulsatile gas and pressurized gas to the breathing head), the pressure supply end of the gas pressure tube and the pulsatile supply end of the pulsatile gas tube terminates in a housing connector having a first connective surface. The terminating tube housing fits in a complementary second connective surface formed in the control housing such that the first and second connective surfaces only interface in a single positional manner. In one embodiment, the first connective surface is D-shaped and the complementary second connective surface in the control housing is an inverse D-shape.

BRIEF DESCRIPTION OF THE DRAWINGS

Further objects and advantages of the present invention can be found in the detailed description of the embodiments when taken in conjunction with the accompanying drawings.

FIG. 3 diagrammatically illustrates that the nebulizer is attached on a depending body base of the breathing head and is fully graphically shown in a rotated 90 degree position and only partly shown in a vertically aligned position, that is, vertically aligned with the depending body plenum (typical during a percussive breathing operation). A storage position is shown when the nebulizer is 90° rotated from the plenum centerline 19A-19B.

FIGS. 9A, B, C and D diagrammatically illustrate the rear cap.

FIGS. 10A, B and C diagrammatically illustrate the nebulizer lid overmold.

FIG. 10D is a partial perspective view of the underside, interior of lid overmold 80.

FIG. 10E shows the nebulizer bowl in an upright position.

FIGS. 11, 12, 13 and 14 diagrammatically illustrate a coupler or connector for breathing head lines (pulsatile gas line and substantially constant gas line) and controller-monitor.

DETAILED DESCRIPTION OF EMBODIMENTS OF THE INVENTION

The percussive ventilation breathing head administers intermittent percussive ventilation to a patient's airway. During an inhalation phase, the patient pulls nebulized aerosol gas into his or her lungs through the percussive ventilation breathing head. During pulsatile gas flow, additional aerosol is provided to the patient during inhalation. During exhalation, pressure sensitive systems in the percussive ventilation breathing head permit exhalation through an exhalation tube in the breathing head.

Figure 1:
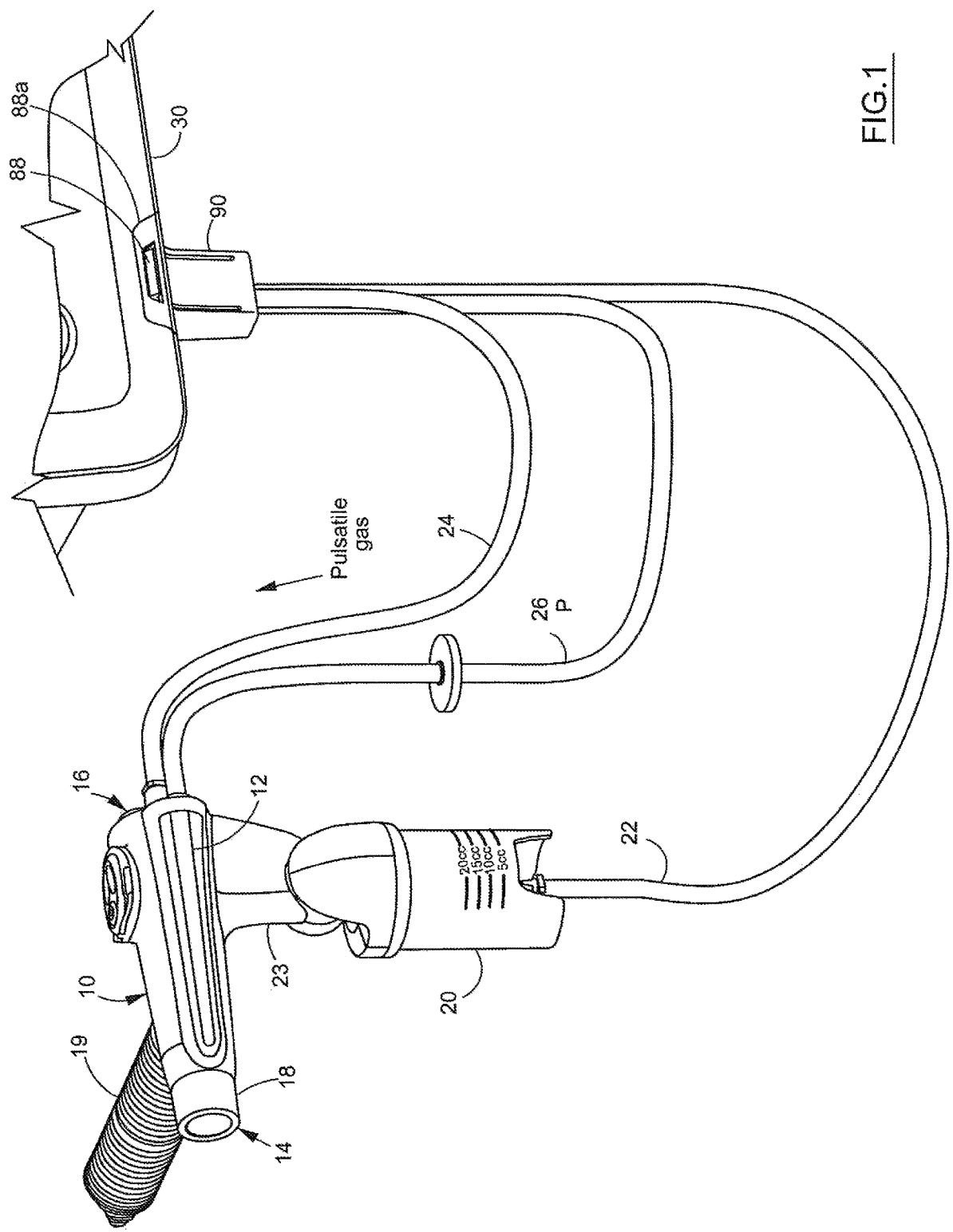
FIG. 1 diagrammatically illustrates the breathing head generally pneumatically coupled to a gas supply and control apparatus 30. The breathing head includes a distal end 14, defined by a mouthpiece, and a proximal end 16.

FIG. 1 diagrammatically illustrates breathing head 10 generally pneumatically coupled to gas supply and control apparatus 30. Breathing head 10 includes a distal end 14 defined by mouthpiece 18 and a proximal end 16. Tube 19 is an extension from the exhalation port not shown in FIG. 1. See exhalation port 50, FIG. 2A. Breathing head 10 includes an elongated view passage 12 and a depending body segment 23 leading to nebulizer 20. A continuous gas supply line 22 is attached to nebulizer 20. A pulsatile gas supply line 24 is connected to an end cap at the proximal end 16 of breathing head 10. Tube 26, coupled at one end to a gas sensor port 53 (FIG. 2A) on the breathing head 10 and coupled to the gas supply and control apparatus 30, permits measurement of gas pressure in the breathing head.

Figure 2A:
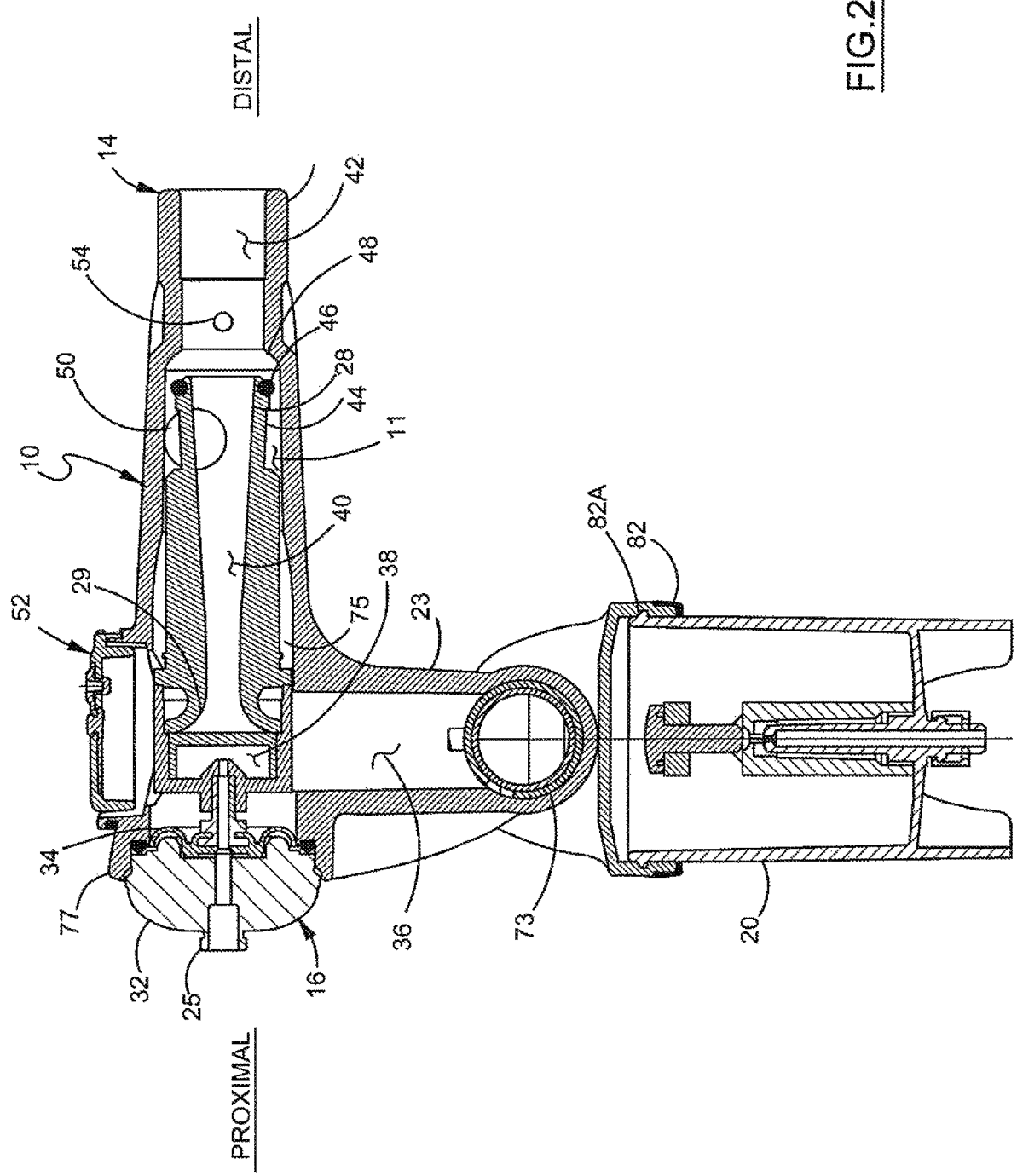
FIG. 2A diagrammatically illustrates a cross-sectional view of the breathing head with a depending body member leading to a nebulizer.

FIG. 2A diagrammatically illustrates a cross-sectional view of breathing head 10 with a depending body member 23 leading to nebulizer 20. Nebulizer 20 is rotatably positioned below depending body member 23 and is removably mounted to depending body member 23. At proximal end 16, an end cap 32 seals off the proximal end of the interior chambers or passageways of breathing head body. A diaphragm 34 is mounted at a distal location on end cap 32. Diaphragm 34 is shown in a collapsed position in FIG. 2A and is shown in an expanded position in FIG. 2B.

Figure 2B:
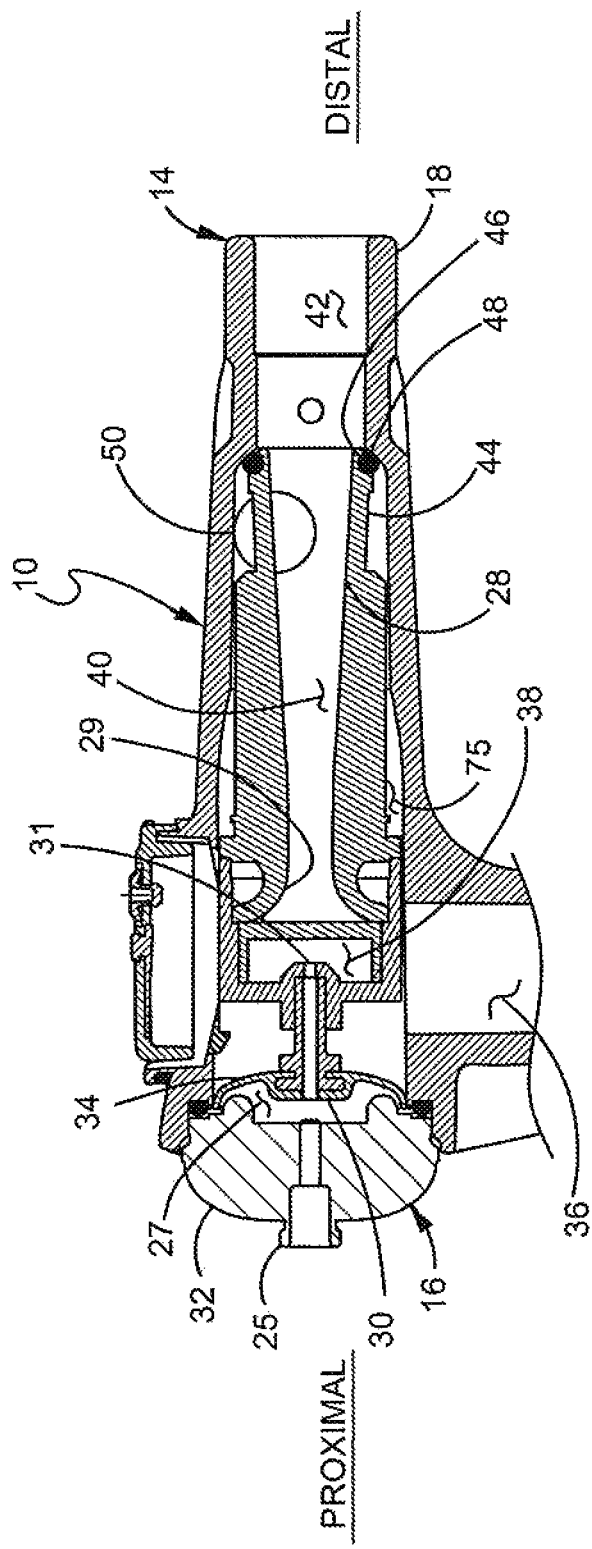
FIG. 2B diagrammatically illustrates injector/shuttle in its distalmost position wherein o-ring is on a valve seat.

In FIG. 2A, injector body or shuttle 44 is generally at its proximal position location. FIG. 2B shows injector/shuttle 44 generally at its distal location wherein O-ring 46 is seated against valve seat 48 formed in the interior passageway of breathing head 10. The terms "distal" and "proximal" are referenced to the hand of the patient holding the percussive ventilation breathing head on or about depending body member 23 during operation, that is, "proximal" being near or closer to the hand of the patient and "distal" referring to items further away from the patient's hand (as a further example, the mouthpiece 18 of the percussive ventilation breathing head 10 is distal to the nebulizer 20 which depends from the breathing head).

Figure 4:
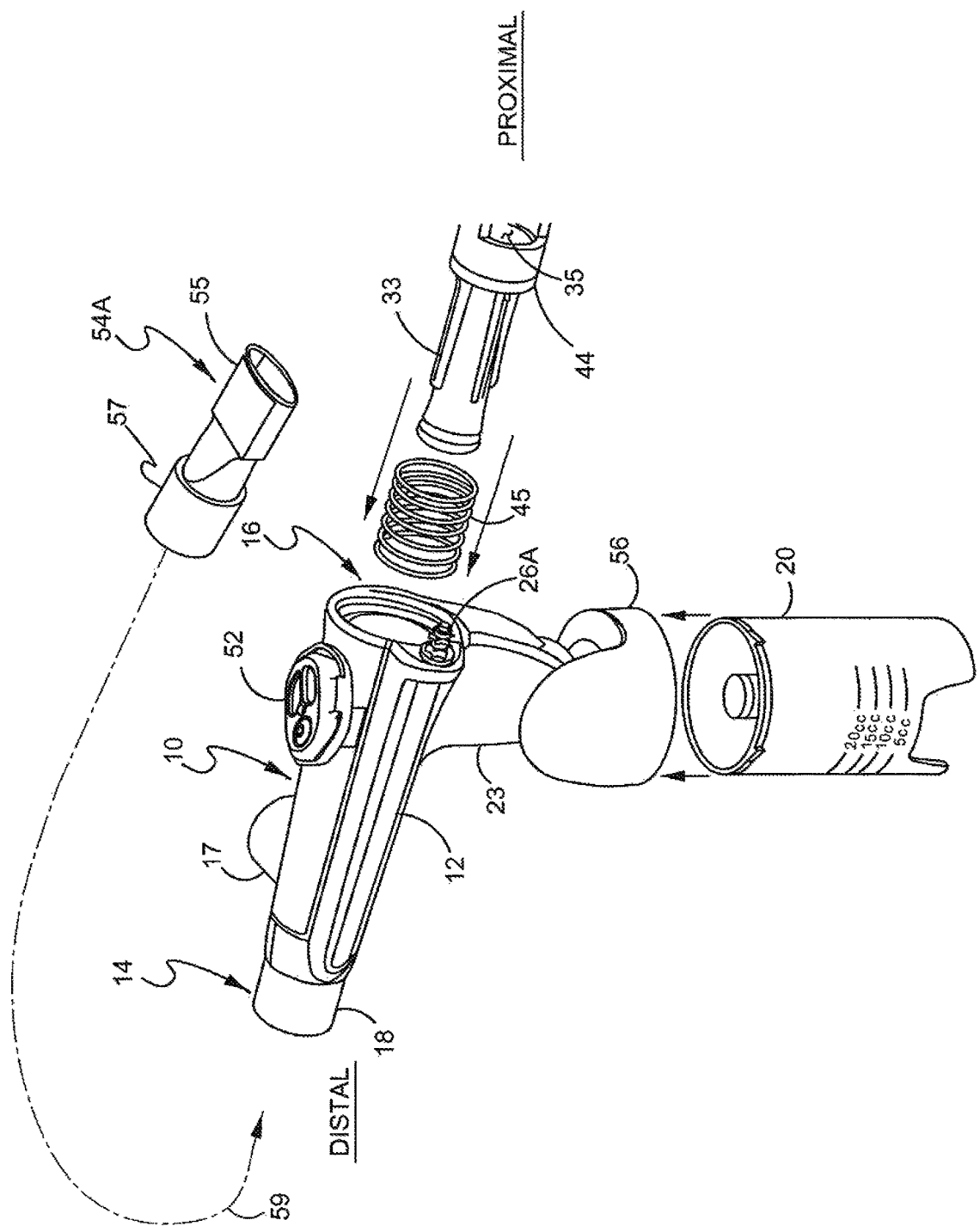
FIG. 4 diagrammatically illustrates the breathing head partly disassembled. The nebulizer is detached from nebulizer lid overmold member.

Gas pulses are fed into proximal chamber 38 from pulsatile gas tube 24. The pulsatile gas tube 24 is connected to aerosol fitting 23 at the proximal side of the breathing head 10. Plenum chamber 36 pneumatically and hydraulically connects (that is, fluidly connects) the interior chamber of nebulizer 20 with the depending body member's plenum 36 and ultimately proximal chamber 38 in breathing head 10. As shown in FIG. 4, injector/shuttle 44 has side ports 35 fluidly connecting plenum chamber 36 with shuttle flow path chamber 40.

Injector or shuttle body 44 defines an interior elongated aerosol flow chamber 40 having variable radial dimensions from a generally narrow proximal region 29 near proximal chamber 38 leading distally towards the distal injector/shuttle region 28 generally near O-ring 46. The proximal flow end region 29 near the venturi-like jet is smaller than the flow region near distal region 28. Hence, distal movement of shuttle 44 injects aerosol into the patient's airway.

Exhalation port 50 is defined on the side of the breathing head body 10. Mouthpiece 18 defines a distalmost aerosol flow chamber 42. A gas sensor pressure port 54 is also defined at a distal location beyond exhalation port 50 in the breathing head body 10.

A unitary entrainment valve 52 is disposed at a generally proximal location on the breathing head body 10 or carried by or upon body 10. Entrainment valve 52 has a valve chamber 63 and is in fluid or pneumatic connection with proximal chamber 38 at the output of the venturi-like jet. Since the aerosol gas flows through the percussive ventilation breathing head are relatively heavily dosed with nebulized particles, reference herein to "fluid connection/communication" or similar words refers to gas with entrained nebulized particles.

FIG. 2B diagrammatically illustrates injector/shuttle 44 in its distalmost position wherein o-ring 46 is on valve seat 48. In this distalmost position, injector/shuttle 44 prohibits all flow through exhalation port 50. Also, pulsatile gas through end cap passage 25 has expanded the proximal chamber 27 on the proximal side of diaphragm 34, moving injector/shuttle in a distal direction while forcing the pulsatile gas flow through narrow channel 30 forming the input channel for venturi-like jet 31. Pulsatile gas tube 24 is attached to aerosol fitting 25 in end cap 32 such that the pulsed gas is fed into first, the proximal diaphragm chamber 27, then through venturi input channel 30 and ultimately into aerosol flow channels 40 and 42. The pulsatile gas ejected from venturi channel 31 carries with it nebulized gas from plenum 36 and nebulizer 20.

Figure 2C:
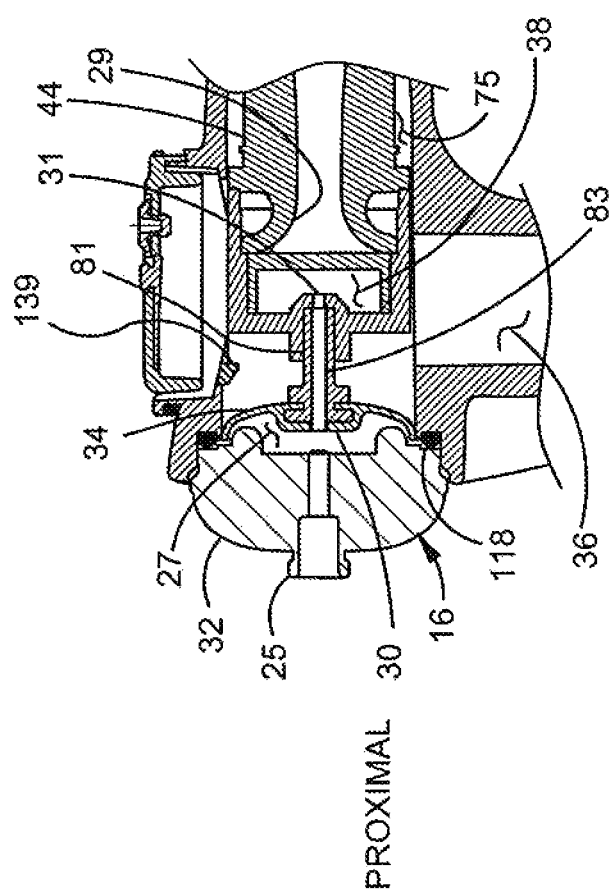
FIG. 2C diagrammatically illustrates a detailed view of the proximal portion of the percussive ventilation breathing head and particularly the venturi-like jet formed nozzle. The shuttle is in its distal most position.

FIG. 2C diagrammatically illustrates a detailed view of the proximal portion of the percussive ventilation breathing head and particularly the venturi-like jet formed at nozzle end 31. In FIG. 2C, pulsatile gas pressure has caused diaphragm 34 to expand proximal diaphragm space 27. The venturi jet sub-system includes a stem 83 which distally extends into channel passage 81 formed at the proximalmost end of the injector/shuttle 44.

Diaphragm 34 has, at its proximalmost portion, a circumferential O-ring type seal ring 118. O-ring seal 118 is seated between a ledge in the proximal region of the breathing head body and ring seal surface 78A in FIG. 9B. Circumferential distally protruding ridge 78 in FIG. 9B captures a complementary diaphragm leg element on the diaphragm 34 as shown in FIG. 2C.

In the disassembled state shown in FIG. 4, although the end cap 70 (FIG. 9A) is not shown removed from percussive ventilation breathing head body, in one construction, the venturi jet sub-system (which includes stem 83) is attached to the proximal end region of shuttle 44, and the diaphragm remains mounted the proximal end of stem 83 (that is, the diaphragm is attached to the venturi-like nozzle). When the end cap 32 is unscrewed via the female threads on the proximal end region of the breathing head body (FIG. 9A), the O-ring seal 118 of the diaphragm is opened and the diaphragm, venturi jet sub-system (which includes stem 83) remains attached to and mounted to the proximal end region of shuttle 44. This diaphragm, venturi jet and shuttle 44, as a single attached sub-system, is then removed (in addition to the spring 45, FIG. 4) from the breathing head body. The diaphragm O-ring seal 118 would then be the proximalmost element on the shuttle sub-system. This is a first construct of the end components.

In a second construction, with attention given to FIG. 2C, the venturi-like nozzle is mounted on the distal side of the diaphragm 34. In the second construct, stem 83 is removable from channel 81 on the proximal side of the shuttle 44. The venturi-like nozzle then remains mounted onto the distal side of the diaphragm. Therefore, at disassembly, the end cap is separated from the diaphragm due the released O-ring seal 118, the diaphragm/venturi-like nozzle is separated from the shuttle 44, the spring 45 is removed from the body of the percussive ventilation breathing head, and then the shuttle 44 is removed from the breathing head body. When constructed, there is a seal between stem 83 and the distal end of channel passage 81.

In a third construct, the venturi-like nozzle is fixedly mounted to the proximal end of shuttle 44 and there is a seal between the proximal end of stem 83 and the distal end of diaphragm 34. In this third construct during disassembly, end cap 32 is unscrewed, O-ring seal 118 is opened, the seal between the proximal end of stem 83 and the distal end of diaphragm 34 is opened, and then the proximal end of the shuttle 44 includes the entirety of the venturi-like nozzle, including stem 83. The venturi-like nozzle and stem 83 is fixedly mounted to the proximal end of the shuttle 44. In the third alternative embodiment, the proximal end of stem 83 is removably seated against a distal seal at an output port of diaphragm 34.

Operationally, the percussive ventilation breathing head administers intermittent percussive ventilation to a patient's airway. In general, the breathing head includes a nebulizer depending from the generally cylindrical headpiece. The breathing head is supplied with a constant pressurized gas (line 22, FIG. 1) which nebulizes liquid contained in the nebulizer unit 22. The nebulizer unit depends beneath the depending body member 23, which in turn is attached below generally cylindrical breathing head body 10. The aerosol from the nebulizer passes through a proximally disposed venturi-like passageway 38, through proximal space 38, flow passages and ports 29, 20 and 42 and into a mouthpiece 18 at a distal end 14 of the breathing head 10 and further into the airway of the patient to begin inflation of the patient's lungs during commencement of the inspiratory phase.

The aerosol generally passes around and through the reciprocating injector body or shuttle 44 movably mounted in the breathing head passageway. The injector body or shuttle 44 includes outboard radial ribs 33 (see FIG. 4) permitting the aerosol to pass over the injector body or shuttle from the proximal location 38 of the breathing head 10 to a distal location 42 which defines the mouthpiece 18 for the breathing head 10. In the event that a coupler 57 (see FIG. 4) is mounted on the mouthpiece 18, the patient's mouth is far removed at a distal location 14 as compared with the patient's hand holding either the depending body member 23 or the nebulizer 20.

To continue with the inspiratory phase with cyclic percussion, pulses of gas are supplied to the percussive ventilation breathing head through a separate pulsatile supply line 24 at a proximal end 16 of the breathing head and these pulses of gas overwhelm the venturi orifice at the proximal end of the breathing head. These pulsatile gases, during a peak gaseous flow cycle, inflate a diaphragm space 27 in the proximal portion of the breathing head to overcome the reactive force in the diaphragm and thereby cause movement of the injector body or shuttle 44 to move in a distal direction 14 toward the mouthpiece 18 causing the distalmost portion of the injector body or shuttle 44 to form a seal with an O-ring 46 against a valve seat 48 in the distal cavity region of the breathing head. At this maximal distal end, the O-ring seals 46 off injector body/shuttle 44 against a valve seat 48 and this seal closes off an exhalation port 50 in the breathing head body thereby delivering a pulse of aerosol laden gas into the patient's lungs. As a result, the pulsatile gases are supplied through the diaphragm-defined space 27 to a venturi input orifice and through the venturi-like passageway 38 and into the patient's airway via the mouth 18 of the breathing head 10.

During the supply of these pulsatile gases, the shuttle or injector body repeatedly reciprocates back and forth between closed and open positions with the valve seat at the proximal end of the breathing head based essentially on the pulsed gas cycles. A spring 45 (FIG. 4) biases the injector/shuttle 44 to a proximal, contracted diaphragm position (FIG. 2A). The percussive ventilation breathing head 10, on one or more interior locations, defines one or more shuttle stops which limit the proximalmost shuttle position. For example, see stop 139 in FIG. 2C. Other stops may be employed. Other biasing systems may be used such as a resilient band or bands, a plurality of springs, springs biasing in both distal and proximal directions, or a pneumatic push-back system porting pressurized gas to the biasing mechanism such as a piston or a secondary diaphragm acting on the shuttle. The application of expanding gas pressure in the pulsatile gas flow expands the diaphragm-defined space 27 and the pulsatile gas is fed through the venturi-like jet to the flow passages 40, 42 while forcing the injector/shuttle 44 against the valve seat 48. The peak portions of the gaseous cycles force the injector/shuttle against the distal breathing head seal 48 and during the lower pressure gas valleys, the proximal diaphragm-defined space behind the injector/shuttle has less pressure and the injector/shuttle 44 moves in the proximal direction thereby opening O-ring/valve at the distal end of the injector/shuttle and further opening the exhalation port 50. The spring 45 assists in the return of the injector/shuttle 44. Hence, the reciprocating shuttle opens and closes the exhalation port 50.

Figure 10D:
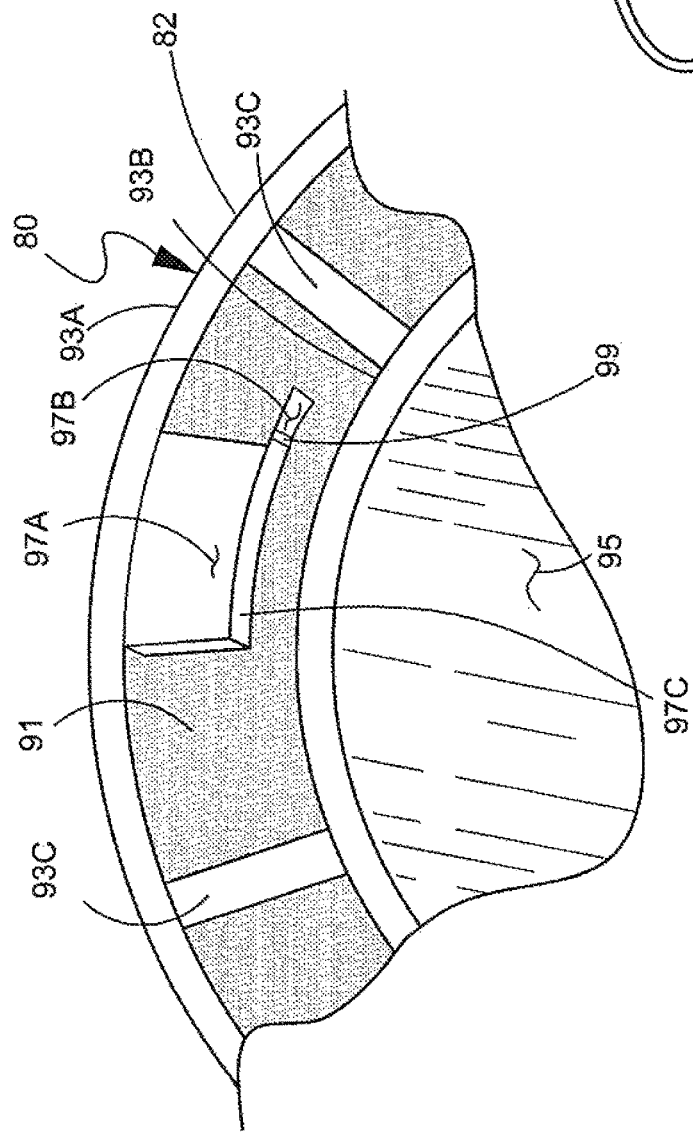
FIGS. 10D and 10E diagrammatically illustrate the nebulizer lid overmold and interlocking tabs on the top rib of the nebulizer bowl.

Although the gases are released through the exhalation port with each opening of the exhalation port, there is only a partial release of the gas from each cyclic pulse until a maximum inflated pressure achieved given the patient's capacity. The maximum inflated pressure is determined by the patient's breathing cycle and lung capacity. This can be measured by pressure sensor port 54, sensor line 26 (FIG. 10) and pressure monitors in gas supply/controller/monitor 30.

A diaphragm 34 is mounted at a proximal position in the breathing head 10 and is also connected to an end cap 32 at the proximal end 16 of the injector/shuttle 44. The injector/shuttle 44 is moved to its distalmost position in the breathing head body 10, by the expanse 27 of diaphragm 34 at the proximal end 16 of the breathing head and by the pulsatile gas pressure at port end 29 of shuttle 44. The shuttle movement reduces spaces 40, 42 filled with aerosol. Thereafter during lower pressure gas cycles, and the diaphragm 34 biases, collapses or pulls back the injector/shuttle away from its distalmost position/valve sealed position and towards the valve open position of FIG. 2A.

As soon as the high-pressure pulse cycle of gas is terminated from the pulsating gas supply line (at the low pressure cycle), the diaphragm 34 with its retracting memory returns the injector or shuttle 44 to its proximalmost position to again open the expiratory port 50 to provide partial release of expiratory gases. Therefore, there is a rapid opening and closing of the expiratory port 50 in accordance with the frequency of the pulsatile gases at certain cyclical rates.

When the patient desires to exhale, the patient exhales against the incoming pulsatile gases and creates a pressure against the proximal diaphragm 34 to overwhelm the forces applied to the diaphragm 34 and move the injector body or shuttle away from the distal valve seat 48 thereby opening the valve at the proximal location (FIG. 2A) of the breathing had body.

During the inhalation phase, at any time that the demand of the patient exceeds the outflow from the nebulizer, ambient air is introduced into flow chambers 40, 42 for mixing with the nebulized aerosol from plenum 36 through a specially designed valve 52 serving as an ambient entrainment gate. This entrainment of ambient air with the aerosol greatly enhances uninterrupted therapeutic aerosol delivery during the inspiratory phase at or near the metered start of the percussive injection of pulsatile gases into the airway the patient. When the physiological airway pressure increases to or beyond the selected fluid clutching pressure (which may be characterized as a venturi stalling pressure) within the injector body or shuttle, the ambient entrainment gate closes 52 and prevents ambient aerosol flushing from the plenum chamber 36 between the nebulizer 20 and the entrainment port 38 of the venturi-like passageway at proximal end 29 of the injector/shuttle 44. This maintains a potential directional flow of aerosol upward in and around the injector body or shuttle 44 to an ambient through the exhalation port 50 at all times.

Figure 7:
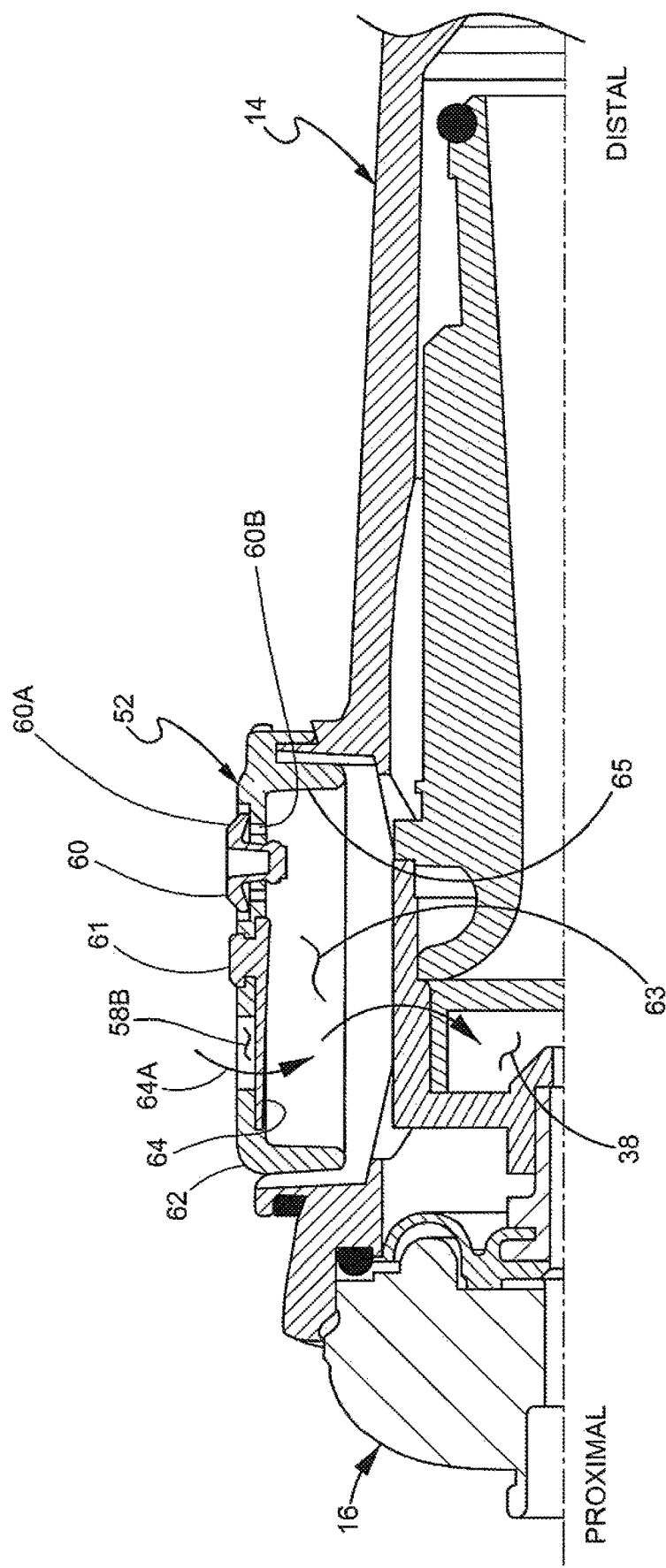

The components of the present invention include breathing head assembly 10, having a distal end 14 and a proximal end 16 (which is farther away from patient mouthpiece assembly 18), a venturi-like chamber 38, and a reciprocating injector body or shuttle 44. The reciprocating injector body or shuttle 44 provides step-wise pulsatile aerosol to the patient. The breathing head assembly 10 includes a hollow body cavity 11 within which the shuttle 44 opens and closes the aerosol flow by coacting against a step valve seat 48 in flow passage 42. The breathing head further includes a pressure sensor port 54 which is an input to a longitudinal view channel 12 leading to a tube 26 which monitors pressure in the flow passage 40, 42. Port 54 is disposed in an upper region of view channel 12. At the proximal end 16, the flow passage 40 has a diaphragm 34 with a retracting memory which, in cooperation with the pulsatile gas flow fed into the flow passage 40 generates or assists the pulsatile and shuttle action of the shuttle 44 in the hollow body breathing head. An entrainment port cap 52 is used to admit ambient air into flow passage 40. The ambient entrainment gate flapper valve 64 is shown in FIG. 7. A nebulizer 20 is attached to a depending body member which defines plenum 36. The breathing head also has an exhalation port 50. When an o-ring 46 at the distal end of the shuttle 44 is seated on valve seat 48, aerosol flow to the exhalation port 50 is blocked (OFF). Fluid flow to exhalation port 50 is dependent upon the longitudinal position of the shuttle 44 in the hollow body of the breathing head.

The resulting breathing head can be made sterile with its biocompatible gas pathway and airway. Further, it is easier to clean open the hollow body with the removable rear cap 32 and withdraw the spring 45 and the shuttle 44. Spring 45 is disposed in percussive ventilation breathing head space 75. In FIGS. 2A and 2B, spring 45 is not shown. The nebulizer 20 can be rotated from the vertical operational position (see FIG. 3, vertical half view at centerline 19A-19B) to a storage collapsed position (see FIG. 3, horizontal full view) with a sealed swivel joint between the depending body segment 23 and the nebulizer canister 20. FIGS. 10A-10E show the swivel joint.

FIG. 3 diagrammatically illustrates that nebulizer 20 is attached on a depending body base 23 of breathing head 10 and is fully graphically shown in a rotated 90 degree position and only partly graphically shown in a vertically aligned position. During the percussive breathing operation, nebulizer is in vertical alignment with plenum 36. For storage, nebulizer is rotated to a second position, 90° rotated from the plenum centerline 19A-19B and depending body base 23. A partial cross-sectional view of the vertically aligned nebulizer 20 is provided to the left of centerline 19A-19B in FIG. 3. In the non-operational position, nebulized body rotated 90 degrees shown in FIG. 3 permits the user to compactly store the breathing head unit when not in use.

FIG. 4 diagrammatically illustrates breathing head 10 partly disassembled. Nebulizer 20 is detached from nebulizer lid overmold member 56. Valve port stem 26A (an aerosol port) is adapted to be coupled to a complementary valve fitting at the end of pressure monitoring line 26 shown in FIG. 1. A transparent viewing passageway 20 is in fluid communication with pressure monitor tube 26 and further with pressure sensing port 54 shown in FIG. 2A. In FIG. 2A, diaphragm 34 is made of medical grade silicone. In the disassembled cleaning mold (FIG. 4) the end cap is unscrewed and removed from breathing head body, the shuttle and shuttle-connected pieces are withdrawn, the spring or biasing elements withdrawn and the body and other components are cleaned.

Spring 45 biases the injector body or shuttle 44 in a proximal position away from valve seat 48 (see FIG. 2A). The injector body 44 and spring 45 can be withdrawn from the interior passageway of the breathing head body for cleaning Exhalation port fitting 17 is in fluid communication with exhalation port 19 shown in FIGS. 1 and 2A.

Supplemental mouthpiece 54 has a proximal end 57 which fits within the mouthpiece 18 defined at distal end 14 of breathing head 10. The supplemental mouthpiece 54 is inserted as shown by arrow 59 into the mouthpiece 18 of breathing head 10 in FIG. 4. Supplemental mouthpiece 54 includes a distal end portion 55 which has an oval orifice. Accordingly, supplemental mouthpiece 54 can be removed to facilitate the cleaning of breathing head 10.

Figure 5:
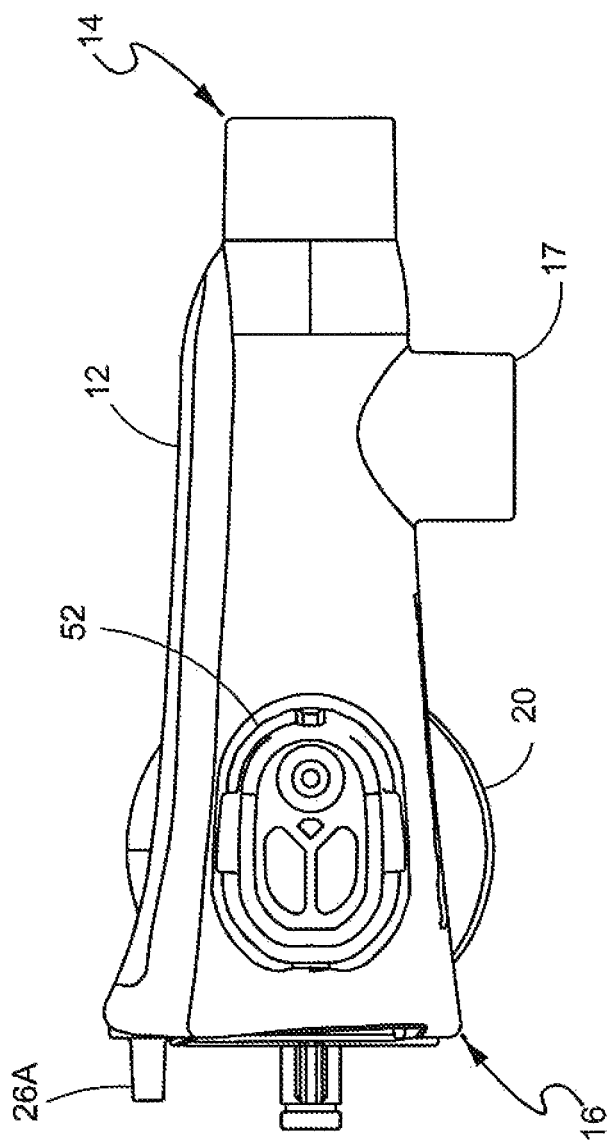
FIGS. 5, 6 and 7 diagrammatically illustrate the integrated flapper entrainment port and two-way valve.
Figure 6:
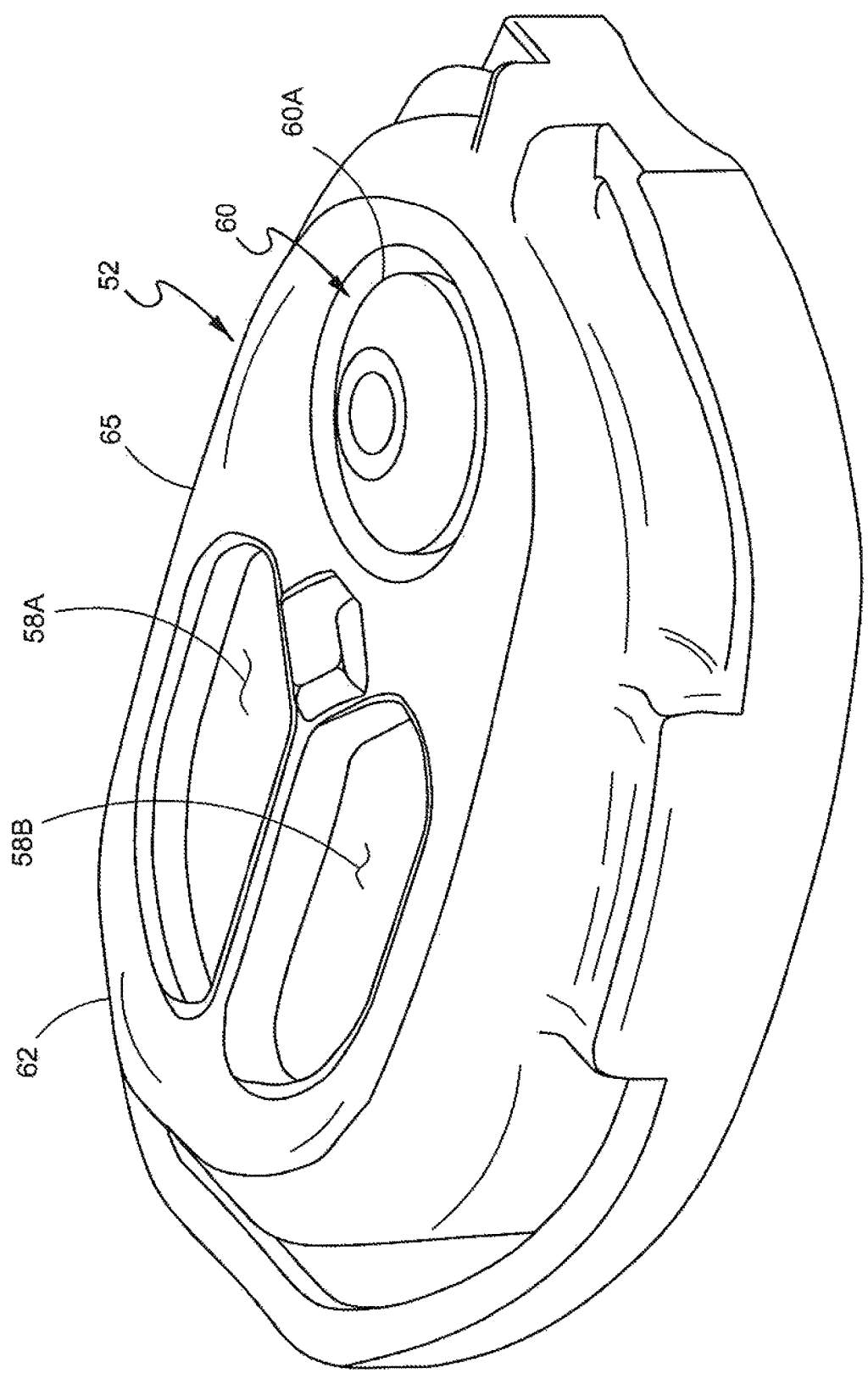

FIGS. 5, 6 and 7 diagrammatically illustrate the integrated flapper entrainment port and two-way valve as unitary entrainment valve 52. This is a new flapper entrainment port and two way valve. FIG. 6 shows cap 62 of entrainment valve body 65 having to apertures 58A and 58B on its top surface. Overpressure valve 60 is shown also on cap 62.

A single unitary entrainment valve is defined one or more apertures 58A, 58B, open to the ambient environment. These apertures are normally closed by a flapper valve member 64 (member 64 shown in FIG. 7) depending below the valve body. Flapper valve member 64 is biased closed against the valve body ridge member between apertures 58A and 58B in FIG. 6 and the interior peripheral lip or edges forming a valve seat with the ridge member or members. Valve chamber 63 is defined by entrainment valve body 65. Ambient air route 64A shows a one-way gas flow system with flow through flapper valve member 64 as caused by the direction of rotation of flapper valve member 64 in FIG. 7. This ambient air further flows, as shown by arrow 64A, through chamber 63 and into the proximal chamber 38 (see chamber 38 in FIG. 2A). In one embodiment, the hinge point for flapper member 64 is the plug 61 at a distal location slightly spaced away from flapper member 64.

The flapper valve member 64 opens when the interior or internal pressure is lower than the ambient pressure during the patient's inspiration cycle. The unitary entrainment valve 62 also includes another aperture (not numbered) into which is mounted one-way over-pressure pop open valve 60. This third aperture is completely filled and blocked by the one-way over-pressure pop open valve 60.

In one embodiment, the over-pressure pop open valve 60 all is configured as an umbrella valve. The umbrella valve 60 opens when the interior or internal pressure exceeds the biased closing force of the umbrella flap 60A surrounding the umbrella valve stem. The umbrella valve 60 has formed therein one or more small apertures. One aperture 60B in shown in FIG. 7. When umbrella flap 60A lifts up due to excessive pressure in the internal chamber 63 immediately below unitary entrainment valve 52 (that is, also interior chamber 38), the flap 60A opens passageway 60B thereby permitting an overpressure excess gas release. There are a number of umbrella valve passageways 60B about the umbrella flap 60A. Valve chamber 63 is defined by entrainment valve body 65.

The over-pressure pop open valve 60 is typically opened when the interior pressure exceeds about 30-40 cm water pressure. The pop open valve 60 is pressure loaded or biased closed such that the umbrella ring flap 60A is biased to a closed position until the interior pressure exceeds the pressure release point for the umbrella valve 60.

Figure 8A:
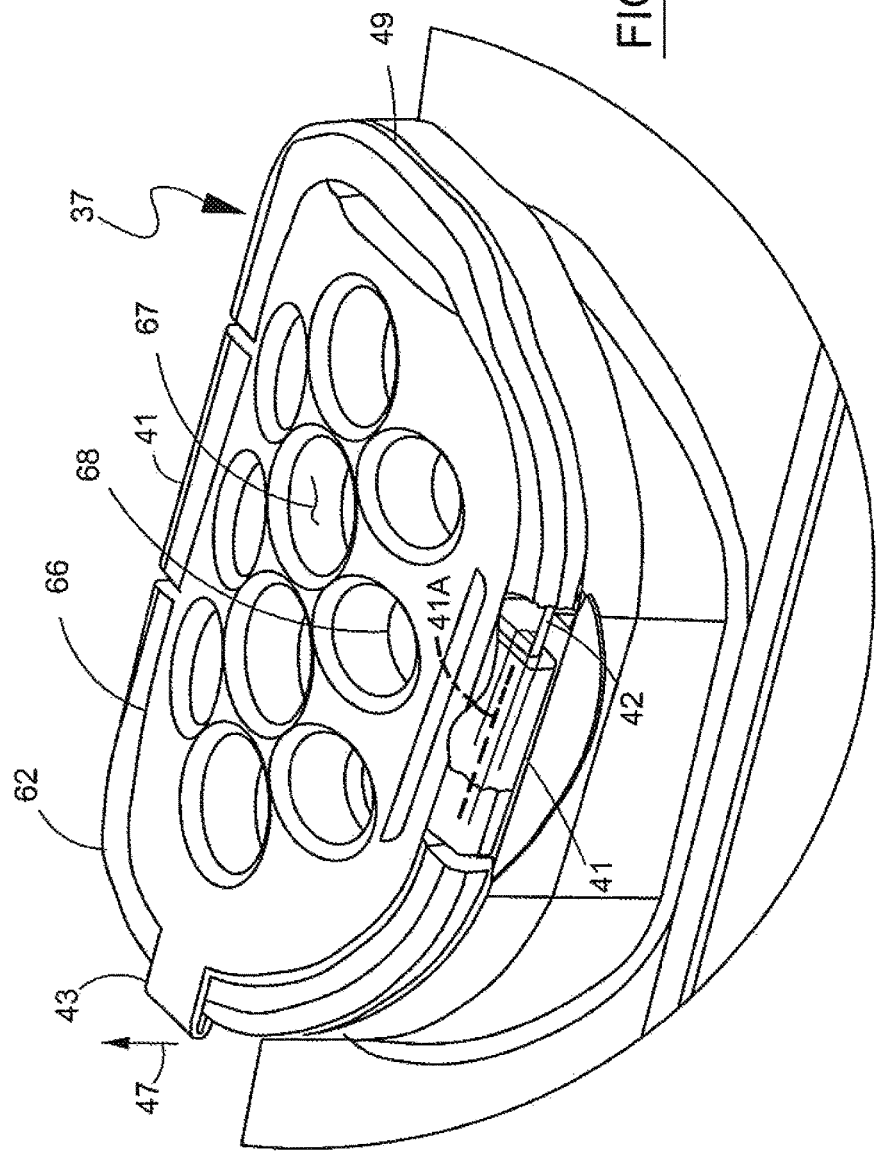
FIGS. 8A and 8B diagrammatically illustrate a different unitary entrainment valve utilizing a hydrophobic filter.
Figure 8B:
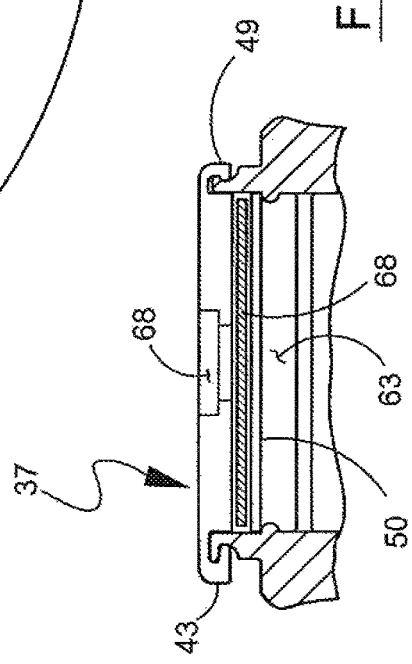

FIGS. 8A and 8B diagrammatically illustrate a different unitary entrainment valve 37 utilizing a hydrophobic filter. The hydrophobic filter element 68 generally repels or fails to interact with the nebulized particles in the aerosol in chambers 64A and 38 (FIG. 7). The flapper valve 64 in the unitary entrainment valve 52 of FIG. 7 can be replaced with a hydrophobic filter 68 shown in the unitary entrainment valve 52 of FIG. 8. The hydrophobic filter 68 is disposed at an interior position beneath apertures 67 in cap 62. The hydrophobic filter subsystem of filter 68 and cap 82 can be supplied to the patient to replace the flapper valve unitary entrainment—over-pressure valve 52 shown in FIG. 7. When a hydrophobic filter is used, there is no need for an over-pressure valve. The hydrophobic filter is put in a cage which snaps into the unitary entrainment valve-overpressure valve snap-in cap 62, as a one-way gas flow system.

Unitary entrainment valve 37 has side clip-over legs 41 which coact and clip-over interior lip 42. Lip 42 protrudes slightly outboard and the inboard leg element 41A of leg 41 protrudes over and then under lip 42. Clip 43 is pulled upward as shown by arrow 47 thereby permitting the release of the opposing, left and right-side leg elements 41A over opposing left and right-side lips 42. At distal end 49 of unitary entrainment valve 37, another latch and latch-lock channel is formed, thereby permitting the complete removal of unitary entrainment valve 37 from the percussive ventilation breathing head 10. The same latch and latch-lock channel closure system is used for unitary valve 52. Therefore, replacement of the valve is easily permitted as well as removal of the valve for cleaning the breathing head.

It is known the hydrophobic filters can permit one-way gas flow. See Millapore http://www.emdmillipore.com/US/en/life-science-research/chromatography-sample-preparation/membrane-learning-center/Flow-Rate/ZMSb.qB.th0AAAFMBEh88eJv,nav.

FIG. 8B shows unitary entrainment valve 37 with the proximal clip-on system 43 and the distal system at distal end 49 of the valve 37. The hydrophobic filter element 68 is mounted at an inboard side of the unitary entrainment valve 37, above chamber 63. A cage or rack 50, having a plurality of apertures therethrough (not shown) retains filter 68 in the unitary entrainment valve 37. To replace filter 68, the user removes unitary entrainment valve 37 from the percussive ventilation breathing head 10, opens the cage 50, removes the old filter 68 and replaces it with a new filter (the new filter placed in the cage and the system snapped back together). Then, the user snaps on the unitary entrainment valve 37 with clip-over legs 41 snapping over interior lip 42. The final snap action is accomplishes with proximal clip 43. In this manner, the hydrophobic filter in the unitary entrainment valve 37 can be replaced either periodically or per use.

FIGS. 9A, 9B, 9C and 9D diagrammatically illustrate the details of rear cap 70. Rear cap 70 includes a user actuation rib 74. In FIG. 2A, end cap 32 is shown. At the centerline of user actuation rib 74 is a male valve port stem 72 (aerosol valve fitting 25 in FIG. 2A) which pneumatically couples the rear cap passageway 72A to pulsatile pressure supply tube 24 shown in FIG. 1. Male aerosol valve port stem 72 cooperates with a complementary female aerosol valve fitting at the terminal end of pulsatile pressure supply tube or line 24.

End cap passageway 72A permits the introduction of pulsatile pressurized air into venturi-like chamber 38 shown in FIG. 2A. Circumferential rib 78 at the distal end of cap 32 retains diaphragm 34 shown in FIG. 2A. Mechanical stop nubs 76A, 76B limit the rotation of rear cap 32 due to complementary stop element 77 shown at the proximal end of breathing head body 10 in FIG. 2A. The sides of rear cap 32 define a threaded surface 79.

The rear cap 32 has a screw surface 79 with stop limiters 76A, 76B, marked to match with stop element 77 (see FIG. 2A). These stop limiters 76A, B provide a visual lock indicator to the user or patient. Visual lock indicator lines 71 on the proximal end of breathing head body are aligned with the user actuatable rib 74. Also, complementary visual markers 71, such as arrows, lines or matching unique visual elements are used which show when the rear member cap 32 is in the full locked position. Other visual indicia may be used. The mechanical stops 76A, 76B on the outside of the screw elements 79 also provide tactile feedback to the user to assure that the end cap 32 is in the fully engaged, locked position.

The percussive ventilation breathing head and end cap include one or more locking mode elements. One locking mode element includes a mechanical stop sub-system formed by cooperating stop elements on said end cap and said percussive ventilation breathing head. See FIG. 9C, stop element 76A and FIG. 2A, stop element 77. Another locking mode element is a pair of visual indicia adapted to the aligned located on the end cap 70 (FIG. 9C), with visual tab element 74 on the end cap 70 and the visual indicia "arrow" 71 on the percussive ventilation breathing head body 10.

A third locking mode element is an audible click lock indicator formed by a pair of complementary detents formed on said end cap and said percussive ventilation breathing head. The audible click lock indicator is similar to the audible and tactile response discussed below in connection with FIGS. 10D and 10E, that is, the sealable interconnection between nebulizer cylinder 20 and the overmold lid 80. In these figures, a small tab 21A, 21B on the nebulizer container 20 passes over generally vertical detent 97A (vertical compared to the lid wall 82 in FIG. 10A). As a result of the flexion of the tab 21A over small detent ridge 99, a tactile indicator is generated as well as an audible indicator.

In the same manner, rear cap 70 may define a small tab in the thread system which passes over a small protruding detent on the percussive ventilation breathing head body 10, generating both an audible click-to-lock indicator and a tactile click-to-lock indicator. The protruding detent and the recessive or channel detent can be formed on either the body 10 of the end cap 70. The tactile click lock indicator is described above as being formed by a pair of complementary detents formed on the end cap and the percussive ventilation breathing head.

The breathing head also includes a patient measuring port with visibility window passage 12. FIG. 1 shows that a visibility window passage runs nearly the entire length of the elongated breathing head 10. FIG. 2A shows pressure sensing port 54 pneumatically and hydraulically in fluid communication with distal passage 42 of the breathing head body. Pressure sensing port 54 is at the distal entry way into visibility window passage 12.

During the breathing cycle of the patient, sometimes aerosol droplets accumulate in the interior head passageway 42 and injector/shuttle passageway 40 because of (a) condensation of the nebulized droplets out of the nebulized aerosol and (b) the two-way patient breathing cycle through the passageways 40, 42. Visibility window 12 permits the patient or user to determine if there is an unacceptable accumulation of mucus or excessive liquid accumulation within the interior passages 40, 42 of the breathing head 10. Further, if there is a drop or a loss of pressure on pressure sensing line 26, the patient or healthcare worker can view the window passage 12 to determine the status of the pressure sensing line and reason for the drop in pressure. Therefore, view passage 12 provides a visual feedback to the patient and care giver.

View passage 12 can be cleaned by inserting a medical grade 3 mm pipe cleaner into the channel once the pressure line 26 (FIG. 1) is uncoupled from the breathing head.

The invention also includes a new overmolded seal for the nebulizer bowl 20 which permits the generally cylindrical nebulizer body 20 to rotate 90 degrees during non-use as shown in FIG. 3. Cylindrical nebulizer body 20 has a nebulizer sub-system 120 therein (see FIG. 3) which receives pressurized gas from tube 22 (FIG. 1) and retains a fluid which the nebulizer sub-system 120 converts into an aerosol. The pressurized gas fed to nebulizer sub-system 120 converts the fluid in a vertically oriented nebulizer canister 20 into nebulized aerosol (a gas heavily laden with liquid particles, called an aerosol herein).

FIGS. 10A, 10B and 10C diagrammatically illustrate the nebulizer lid overmold 80. Depending rim wall 82 of lid 80 has a snap-in configuration 82A (see complementary snap-in fitting in FIG. 2A) which permits the nebulizer bowl 20 to snap into the depending rim 82 of nebulizer lid overmold 80. Lid cover 80 includes a vertical wall 85 (when in the operational position of FIG. 3, wall 85 is vertical compared to depending body 23 centerline 19A-19B) and a male threaded screw 84 which protrudes substantially 90 degrees out from the vertical wall 85. Male threaded screw 84 is complementary to a female screw 73 (FIG. 3) at the bottom of the depending body member 23 defining plenum 36. Screw thread 84 provides a sealed swivel joint between the lid 80 and the depending body 23 forming plenum 36. The sealed swivel joint permits nebulizer 20 to be vertically aligned with plenum 36 as shown in FIG. 2 at centerline 19A-19B and permits the nebulizer 20 to be rotated 90° with respect to plenum 36 is shown in FIG. 3. The nebulizer 20 can swivel substantially 150 degrees from the horizontal, storage position. FIG. 3 shows the nebulizer cannister 20 in a vertical, 90 degree angular position, that is angle 21, from the horizontal, storage position but the cannister can swing further to the left an additional 60 degrees. This additional angle permits the breathing head to be positioned at a number of different angular positions while the nebulizer cannister 20 is vertically positioned relative to a ground plane for optimal operations (stated otherwise, the breathing head can be positioned at many different angular positions while the nebulizer cannister 20 is maintained substantially vertically oriented).

The fluid or aerosol flow through the overmold lid 80 includes a vertical flow through lower lid chamber 122 (when nebulizer 20 is vertically oriented as shown at centerline 19A-19B in FIG. 3) from the interior chamber 121 of nebulizer cylinder 20. The flow then moves through vertical passageway 124 in overmold lid 80 in FIG. 10B. FIG. 10B is a cross-sectional view of the lid 80 from the perspective of view line B'-B" in FIG. 10C. The aerosol from vertical chamber 124 then moves to horizontal lid chamber 126 which is inboard of threads 84.

The new overmold nebulizer bowl seal eliminates the common O-ring that was typically utilized in connection with obtaining a hydraulic and pneumatic seal between the nebulizer unit and the depending body defining plenum 36. The current nebulizer lid overmold 80 has interlocking male and female screw thread threads that involve a click turn. The click turn seal/lock provides both tactile confirmation to the patient or care giver that the nebulizer body 20 is securely mounted on the overmold lid 80 and an audible indicator of the same.

FIGS. 10D and 10E diagrammatically illustrate the nebulizer lid overmold 80 and the interlocking tabs 19A, 19B on top rib 19 of nebulizer bowl 20. FIG. 10D is a partial perspective view of the underside, interior of lid overmold 80 (FIG. 10D looks upward into the underside of overmold 80). The inboard portions of overmold lid wall 82 include an inboard peripheral wall surface 91 having thereon circumferential rings 93A, 93B. Circumferential rings 93A, 93B are stabilized by several inboard extending vertical struts 93C. The peripheral wall surface 91 is shaded in FIG. 10D. The interior space defined by the peripheral wall surface 91 is shown as spacial region 95 in FIG. 10D.

Periodically along the peripheral wall surface 91 of the overmold lid wall 82, are a number of vertical detent channels 97A (hollowed-out spaces). Detent channels 97A are formed on the inboard wall surface 91. The upper region of detent 97A near upper detent wall-limit 97C leads to a partial arcuate channel 97B, formed as a partial circumferential arc in the wall surface 91. There is a angular offset of the partial circumferential arc 97B compared to the generally vertical detent 97A which enhances the fluid seal between the nebulizer peripheral edge ring 19 and the inboard circumferential ring 93B in the overmold lid 80. The angular offset tightens the seal between edge lip 19 and lid ring 93B.

The partial channel-like arc 97B is structurally defined by and also physically defined by a small inboard extending demarcation ridge 99 between partial arcuate peripheral channel 97B and the generally vertical detent 97A (vertical compared to the lid wall 82 in FIG. 10A).

Figure 10E:
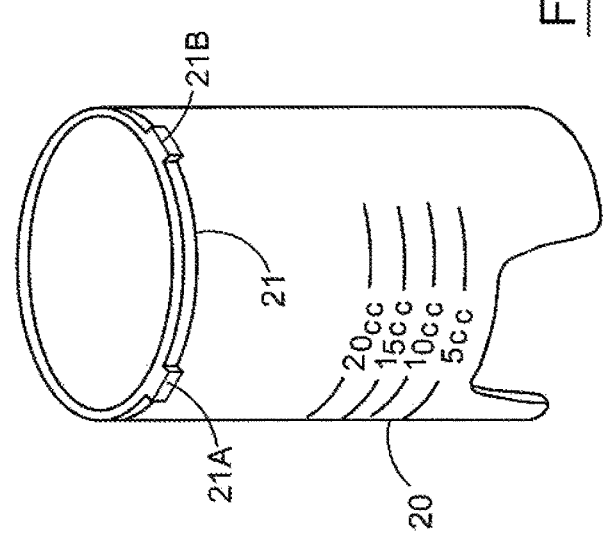

FIG. 10E shows nebulizer bowl 20 in an upright position. Bowl 20 has an upper peripheral ring 19 and a series of outboard extending nubs or tabs 17. Nubs or partial screw-thread-acting tabs 19A, 19B are placed within detent 97A of the lid overmold 80. To assemble the nebulizer bowl 20 onto overmold lid 80, bowl tabs 17 are inserted upwards into detents 97A and until the tabs 19A, 19B reach the upper end detent wall limit 97C of detent 97A, that is, near or adjacent upper detent wall limit 97C. When the nebulizer bowl 20 is rotated, the tabs 19A, 19B pass over small ridge 99 (creating an audible and a tactile response) and thereby permit the bowl 20 to be screwed onto and sealed onto the overmold lid 80 when each tab is moved into partial circumferential detent channel 97B. In this manner, detent channel 97B forms the female screw thread channel for partial screw-thread tabs 19A, 19B.

FIGS. 11, 12, 13 and 14 diagrammatically illustrate the one-way breathing head line and controller coupler or connector. The invention also includes a one-way tube or line connection from the breathing head to the gas supply and control apparatus 30. That one-way tube or line connector 90 (FIG. 11) only permits connection one way to the supply and control apparatus 30 (particularly control housing 69), thereby improving safety. The one-way breathing head line and controller coupler or connector is diagrammatically illustrated in FIGS. 11, 12, 13 and 14.

Gas supply, pressure controller and control monitor 30 is shown in FIG. 1 and the control housing 69 of controller/gas supply/monitor 30 includes a D-shaped female port 86. The female port 86 is complementary to terminal line male plug 86A. The terminal ends of the pressure supply lines 22, 24 and pressure monitoring line 26 terminate in complementary D-shaped male plug 86A. Line or tube 24 carries pulsatile gas to the percussive ventilation breathing head wherein line 22 is a constant supply of gas to the nebulizer 20. On the connector or coupler 90, an outboard extending rim 87 has a semi-flexible clip lip 88 which is biased outboard or away from rim 87 of D-shaped coupler 86A. Flexible lip 88 is at the end of leg 93, thereby permitting the clip lip 88 to move inboard into connector 90 or outboard into clip channel 88A on housing 69 of the supply/controller/monitor 30. Clip 88 fits within clip channel aperture 88A of controller housing 69. The terminal end of the coupler-connector also includes a body 90 which gathers together the terminal ends of tubes 22, 24 and 26. The D-shaped male coupler 86A can only fit one way into the D-shaped female aperture 86 due to the flat side of the D-shaped coupler and the generally semi-circular side of coupler 86A.

Figure 12:
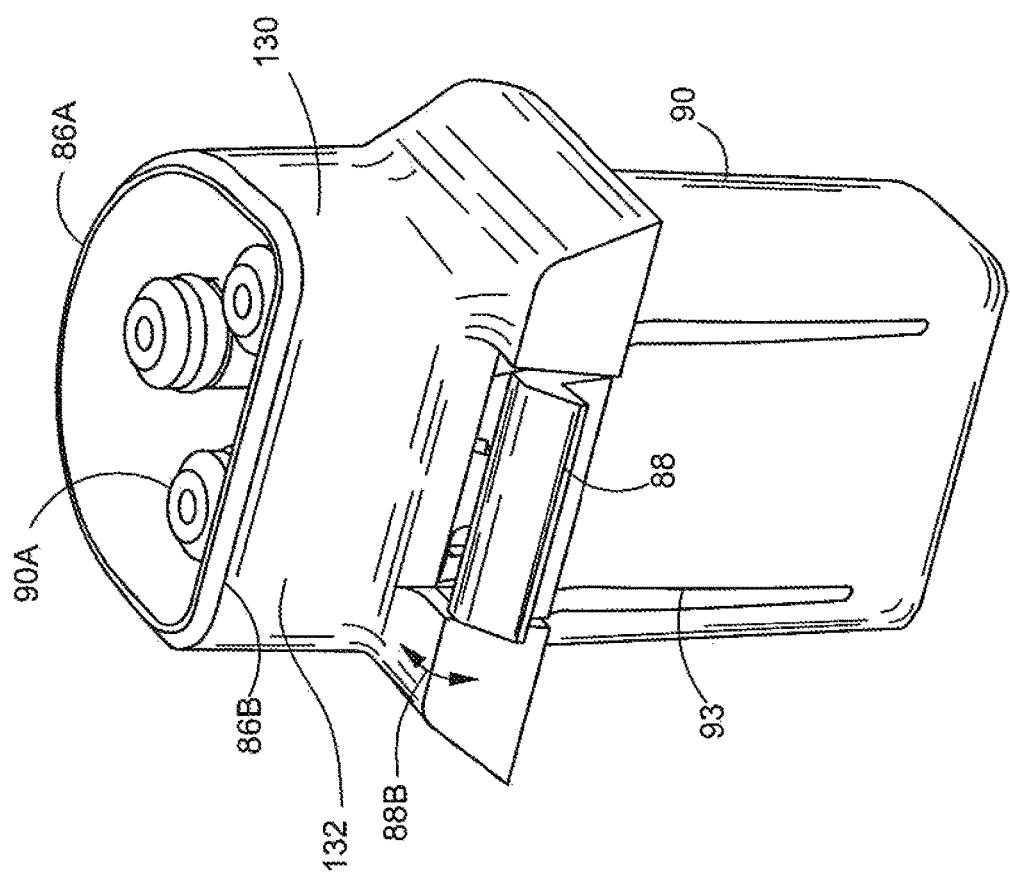

FIG. 12 shows connector 90 and D-shaped male coupler 86A and flat side 86B. FIG. 12 also shows male terminal aerosol valve end couplers 90A for each of the two pressure lines 22, 24 and the pressure monitor line 26. Clip 88 moves back and forth as shown by arrow 88B.

Figure 13:
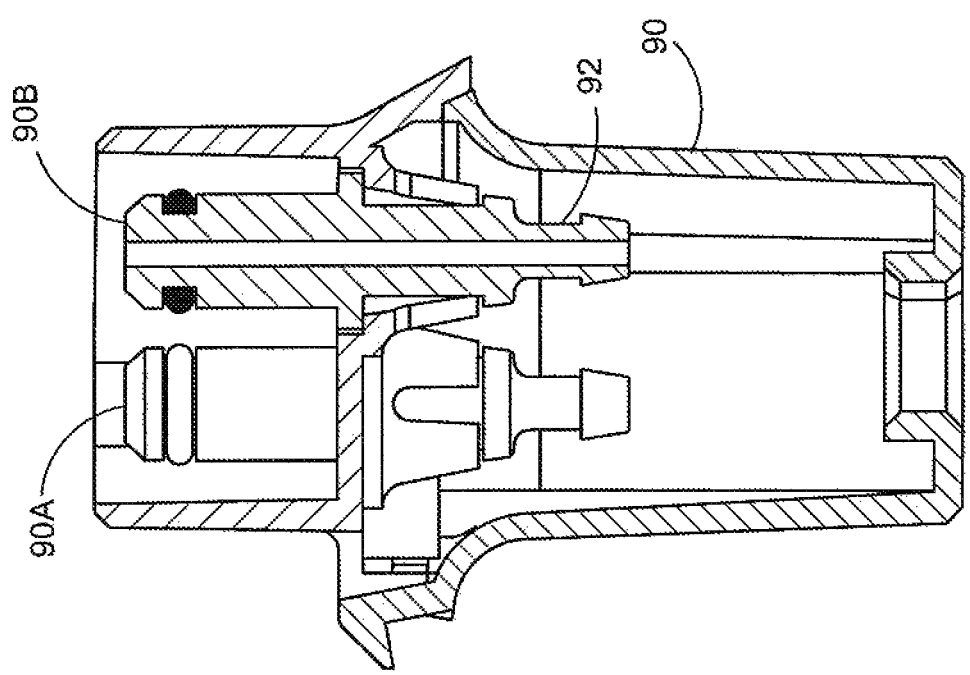

FIG. 13 shows a cross-section of one male aerosol valve fitting 90B retained in an inboard region of the D-shaped coupler 90 and another view of another male aerosol valve fitting 90A. Each of these male valve fittings have O-rings to provide a secure seal with the female fittings on the underside of housing 69 of controller-monitor 30. The depending ends 92 of these valve fittings 90A, 90B are one-way coupling attachments to pressure and sensor tubes 22, 22, 24 and 26.

Figure 14:
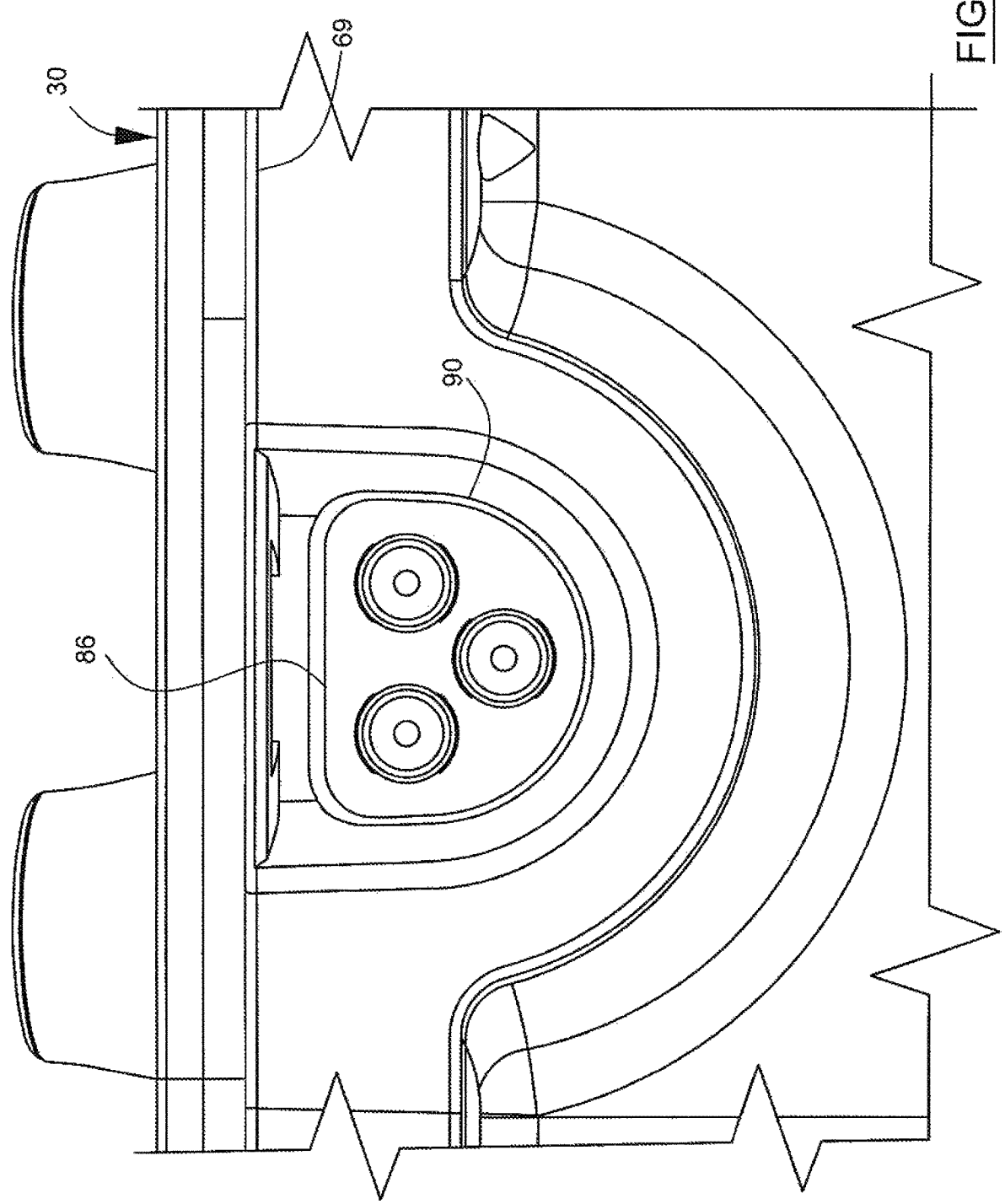
Figure 15:
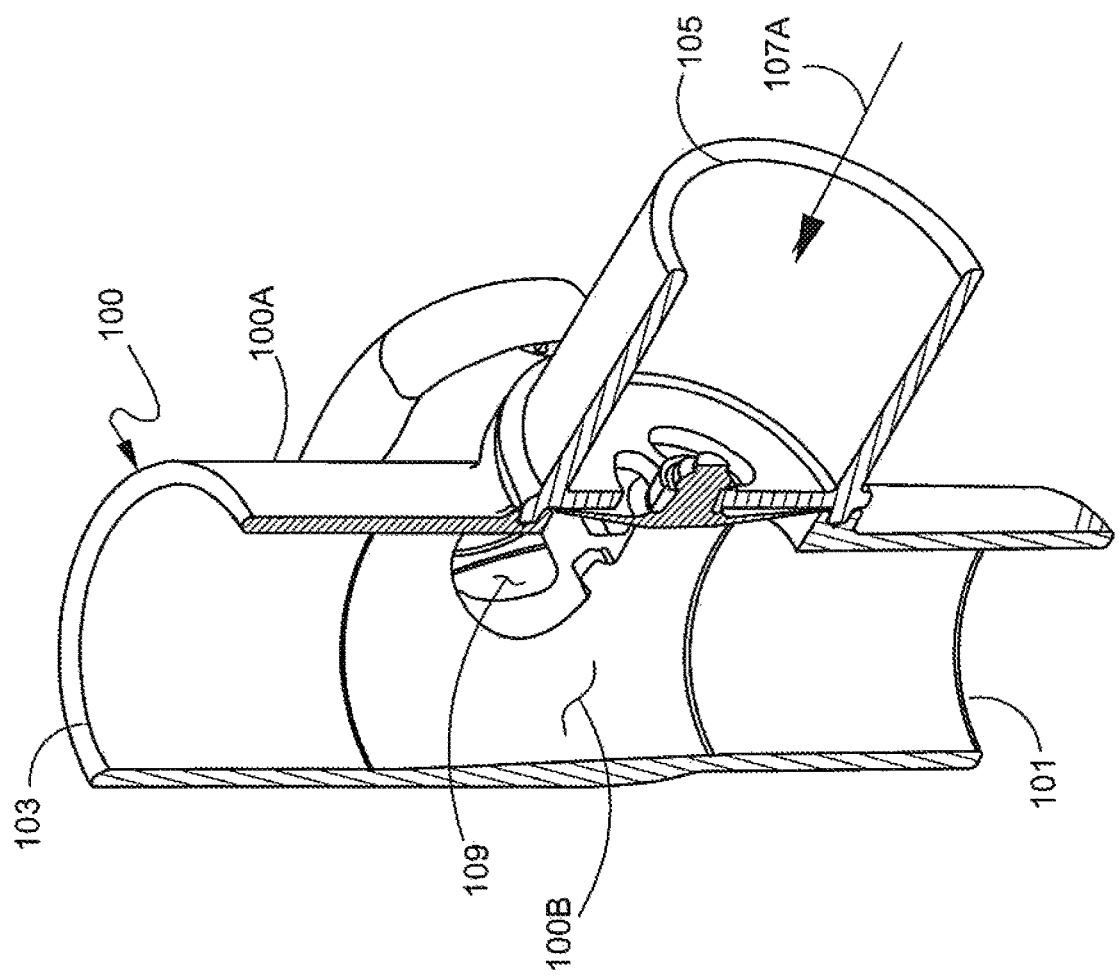
FIGS. 15, 16, 17, and 18, diagrammatically illustrate an interface connection piece permitting the breathing head to be coupled to a conventional ventilator line (and the associated ventilator) for continuing patient treatment such that the breathing head delivers nebulized aerosol pulsatile gas flow during the continuing patient treatment.

FIG. 14 shows the female D shaped coupler 90 and rim 86 on the underside of housing 69 of controller 30 and diagrammatically illustrates the female valve fittings complementary to the male valve fittings.

FIGS. 11, 12, 13 and 14 illustrate a pressure supply end of the gas pressure tube 22 and the pulsatile supply end of the pulsatile gas tube 24 terminating in housing connector 90. Connector 90 has a first connective surface 86A, formed of curved surface 130 and flat surface 132, adapted to fit within a complementary second connective surface formed in the control housing 69 (that is the matching curved surface and matching flat surface in the underside of controller 30). The first connective surface 86A (a combination of surfaces 130 and 132) and the second connective surface 86 only interface in a single positional manner. The curved surface 130 matches a contra-curved surface beneath housing 69 of controller 30 and the flat surface 132 matches a flat surface beneath housing 69. Other first connective surfaces 86A can be formed to match complementary second connective surfaces 86, such as trapezoidal shapes, elliptical shapes, quadrilateral shapes, triangular shapes with unequal sides, etc.

FIGS. 15, 16, 17, and 18, diagrammatically illustrate an interface connection piece permitting the breathing head 10 and particularly mouthpiece 18 to be coupled to a conventional ventilator for continuing patient treatment such that the breathing head delivers nebulized aerosol pulsatile gas flow during the continuing patient treatment.

Interface coupler 100 has an input port 101 and an output port 103 that is connected to conventional ventilator lines or tubes. The input to these ventilator lines or tubes (not shown) is attached to an output of a ventilator machine (not shown). Output port 103 is connected to a typical output tube (not shown) leading to the patient being treated. The interface coupler body 100A has a coupler through channel 100B defined between coupler input port 101 and coupler output port 103. The coupler input and output ports are adapted to be coupled into the ventilator line. Interface coupler 100 has a pulsatile flow port coupler 105 shaped such that the distal mouthpiece assembly 18 of the breathing head 10 (FIG. 2A) can be inserted into the pulsatile input port 105 by inserting the mouthpiece assembly 18 in the direction shown by arrow 107A into the pulsatile input port 105. The operation of the pulsatile input port is substantially identical as discussed above. The pulsatile flow port coupler input port 105 is to be placed in fluid communication with the distal shuttle output flow port 42 (FIG. 2A).

Figure 16:
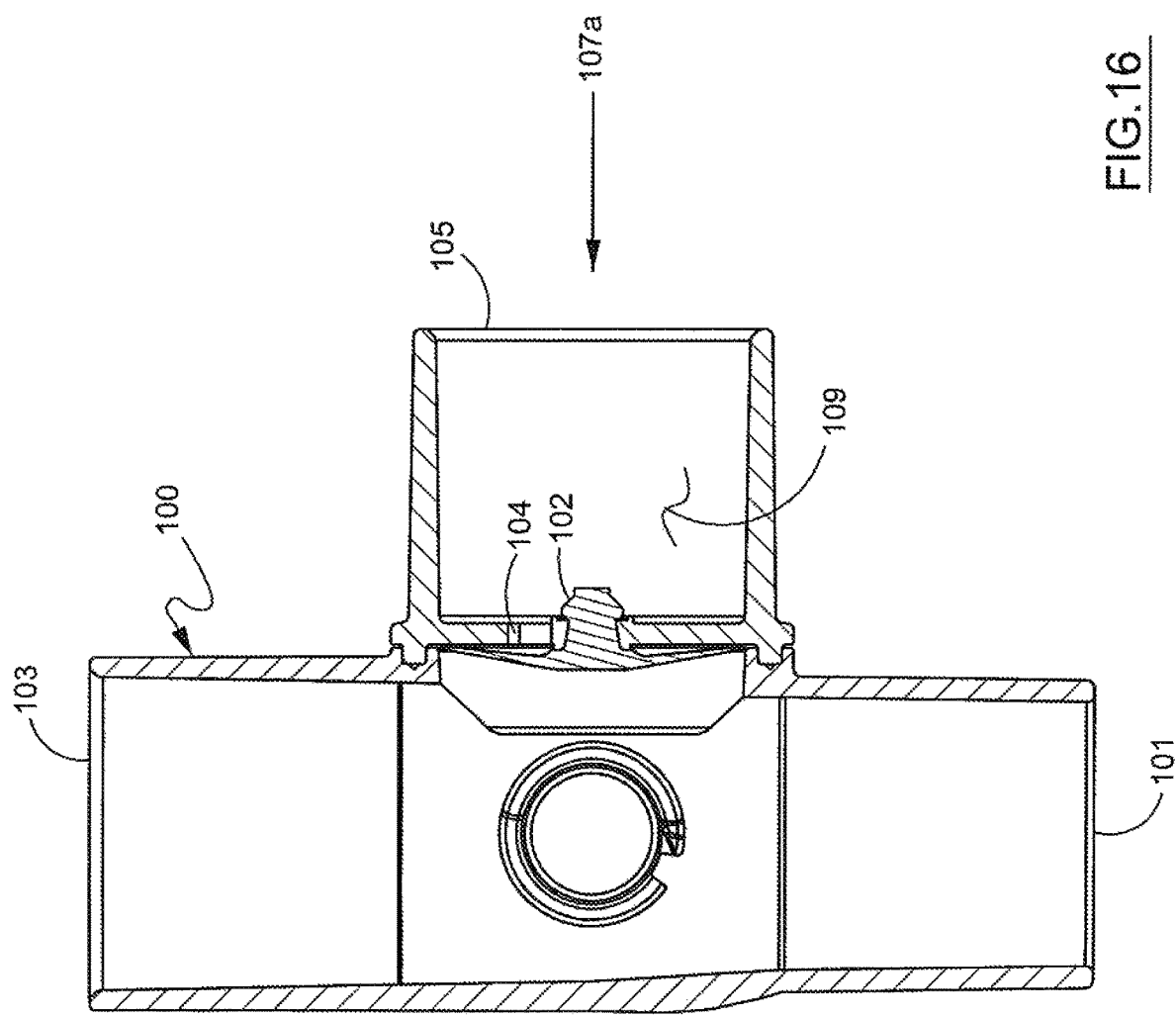

FIG. 16 shows that an umbrella valve 102 that permits one way flow through valve aperture(s) 104 dependent upon the pressure developed by the breathing head in pulsatile input channel 109.

Figure 17:
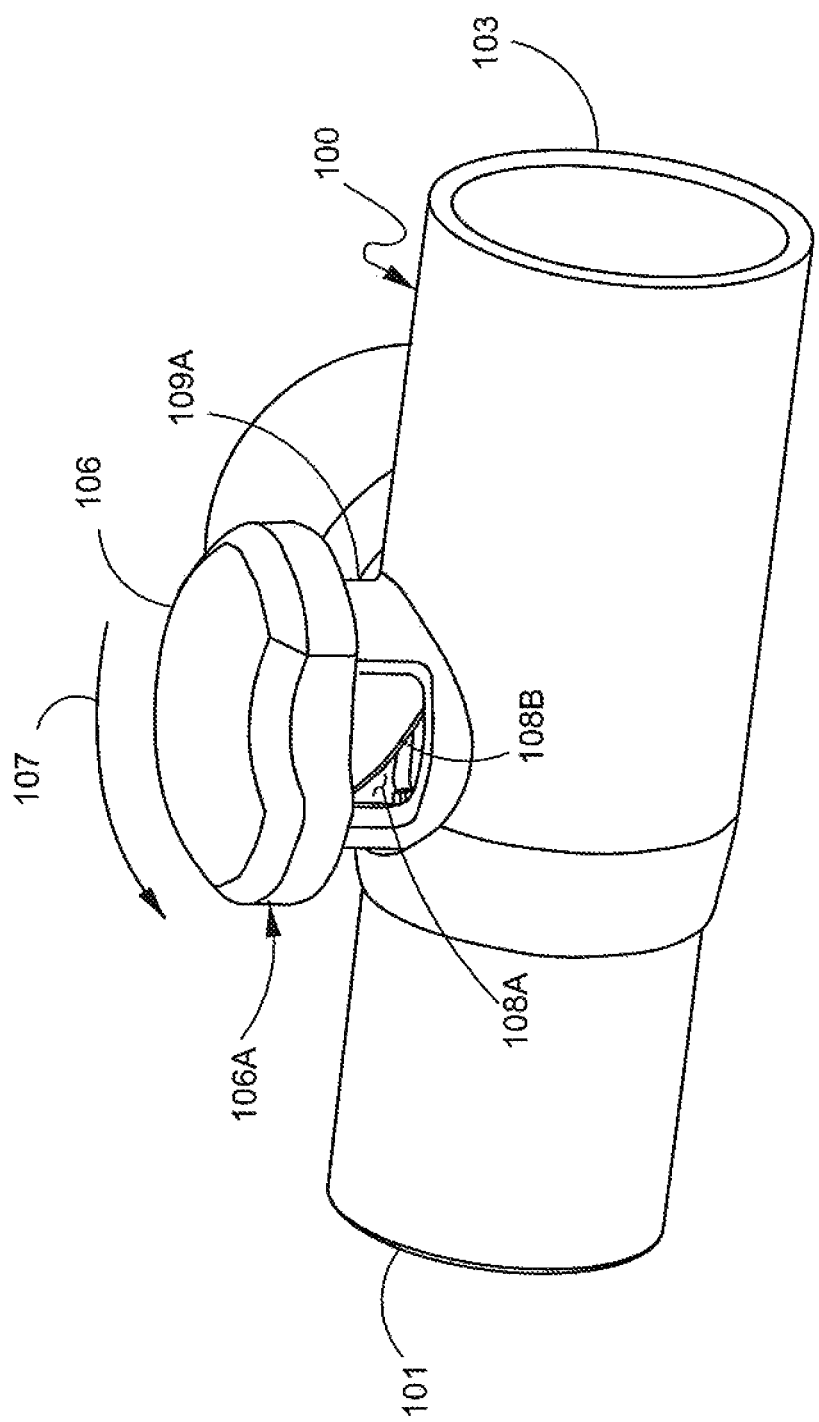

FIG. 17 diagrammatically illustrates that supplemental air can be introduced into the ventilation coupler 100 by a supplemental air valve 106A between input port 101 and output port 103 of through channel 100B by rotating knob or valve stem 106 in the direction shown by arrow 107. There are other valve stems or valve controls may be used, other than a rotating knob valve stem. The supplemental air valve body 109A (FIG. 17) defines a pulsatile channel 109 (FIG. 15) which is open to coupler through channel 100B. The supplemental air valve 106 has a variable valve control stem 108B between a supplemental air vent 108A open to the ambient and coupler through channel 100B. Direction 107 opens the supplemental air valve whereas rotation in the opposite direction closes changeable aperture 108A. The introduction of supplemental air reduces the pressure in the conventional ventilation lines, thereby permitting the pulsatile nebulized aerosol to flow through pulsatile channel 109 (FIG. 15), open the umbrella valve and into the ventilation flow and out output port 103. A flap valve may replace umbrella valve 102.

Figure 18:
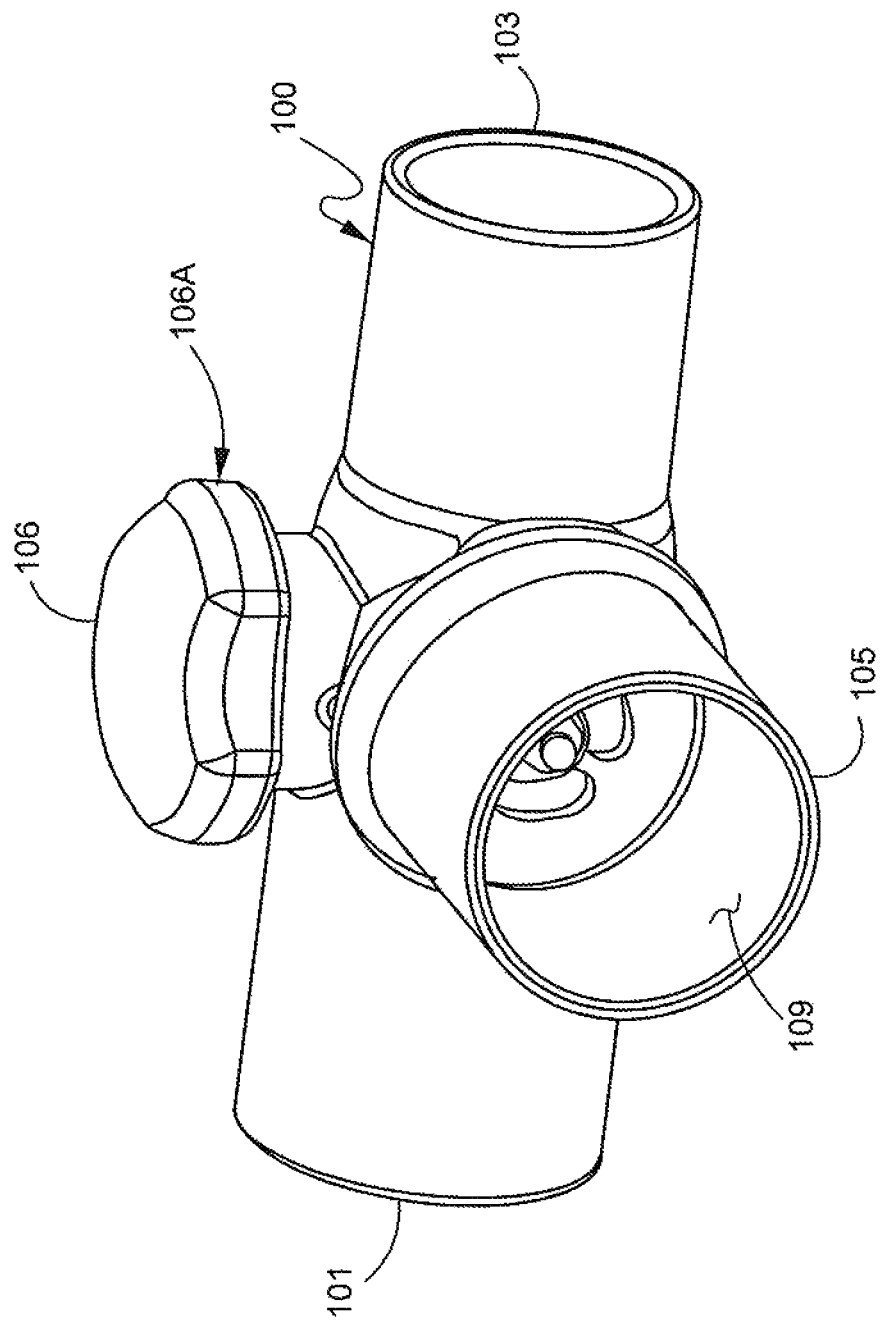

In FIG. 17, valve stem 109 has an aperture 108A in the coupler wall and a rotatable flow control panel 108B that opens and closes aperture 108A dependent upon the position of knob 106. Aperture 108A is shown partly open in FIG. 17. FIG. 18 shows another view of the interface coupler 100.

The claims appended hereto are mean to cover modifications and changes within the scope and spirit of the present invention.

The invention claimed is:

1. A percussive ventilation breathing head adapted to be supplied with a flow of pulsatile gas comprising:
   a breathing head body adapted to be supplied with the pulsatile gas flow at a proximal end of the breathing head, wherein said proximal end is close to a source of pulsatile gas flow supply, and said breathing head body defining an interior passageway in said breathing head body;
   a reciprocating injector shuttle movably mounted in said interior passageway, said shuttle adapted to move distally due to said pulsatile gas, said shuttle biased in a proximal direction within said interior passageway and adapted to move proximally due to said bias, said shuttle defining an internal flow passage from a proximal shuttle input port to a distal shuttle output port;
   a unitary entrainment valve on said breathing head body having an entrainment valve body defining an entrainment valve chamber, said entrainment valve chamber in a top portion of said breathing head body and in fluid communication with said proximal shuttle input port, a valve flapper on said entrainment body biased closed and separating an ambient environment from said entrainment valve chamber; and
   an over-pressure valve on said entrainment valve body adapted to release aerosol to said ambient at a predetermined pressure.

2. The percussive ventilation breathing head as claimed in claim 1 including an elongated spring biasing said shuttle proximally against a shuttle stop defined in said interior passageway.

3. The percussive ventilation breathing head as claimed in claim 1 wherein said over-pressure valve is an umbrella valve intermediate said ambient and said entrainment valve chamber.

4. The percussive ventilation breathing head as claimed in claim 1 wherein said unitary entrainment valve is removably attached said breathing head body.

5. The percussive ventilation breathing head as claimed in claim 1 including an interface coupler adapted to be coupled to a ventilator line between a conventional ventilator and a patient for continuing patient treatment, said interface coupler having:
   an interface coupler body;
   said interface coupler body having a coupler through channel defined between a coupler input port and a coupler output port, said coupler input and output ports adapted to be coupled in said ventilator line; and said interface coupler body having a pulsatile flow port coupler in fluid communication with said coupler through channel via a one-way flow valve mounted in said pulsatile flow port coupler; and, said pulsatile flow port coupler in fluid communication with said distal shuttle output port.

6. The percussive ventilation breathing head as claimed in claim 5 including a supplemental air valve with a supplemental air valve body open to said coupler through channel, said supplemental air valve having a variable valve control stem between a supplemental air vent open to the ambient and said coupler through channel.

7. A percussive ventilation breathing head adapted to be supplied with a flow of pulsatile gas and, independently, a flow of nebulized aerosol fluid comprising:

a breathing head body adapted to be supplied with the pulsatile gas flow at a proximal end of the breathing head, wherein said proximal end is close to a source of pulsatile gas flow supply, and said breathing head body defining an interior passageway in said breathing head body;

a depending plenum from said breathing head body adapted to receive said nebulized gas flow;

a reciprocating injector shuttle movably mounted in said interior passageway, said shuttle adapted to move distally due to said pulsatile gas, said shuttle biased in a proximal direction within said interior passageway and adapted to move proximally due to said bias, said shuttle defining an internal flow passage from a proximal shuttle input port to a distal shuttle output port, said shuttle input port in fluid communication with said depending plenum;

an entrainment valve carried by or upon said breathing head body with an entrainment valve body defining an entrainment valve chamber, said entrainment valve chamber in a top portion of said breathing head body, separate from the depending plenum, and in fluid communication with said proximal shuttle input port, the entrainment valve body carrying a valve flapper biased closed and separating an ambient flow into said entrainment valve chamber and carrying an over-pressure valve adapted to release aerosol to the ambient at a predetermined pressure.

8. The percussive ventilation breathing head as claimed in claim 7 wherein said entrainment valve flapper opens during an inhalation phase.

9. The percussive ventilation breathing head as claimed in claim 7 wherein said unitary entrainment valve is removably attached said breathing head body.

10. A percussive ventilation breathing head adapted to be supplied with a flow of pulsatile gas and, independently, a flow of nebulized aerosol fluid comprising:

a breathing head body adapted to be supplied with the pulsatile gas flow at a proximal end of the breathing head, wherein said proximal end is close to a source of pulsatile gas flow supply, and said breathing head body defining an interior passageway in said breathing head body;

a depending plenum from said breathing head body adapted to receive said nebulized gas flow;

a reciprocating injector shuttle movably mounted in said interior passageway, said shuttle adapted to move distally due to said pulsatile gas, said shuttle biased in a proximal direction within said interior passageway and adapted to move proximally due to said bias, said shuttle defining an internal flow passage from a proximal shuttle input port to a distal shuttle output port, said shuttle input port in fluid communication with said depending plenum; and an entrainment valve carried by or upon said breathing head body having an entrainment valve body having one or more apertures covered with a hydrophobic filter between an ambient to an entrainment valve chamber in a top portion of said breathing head body and said entrainment valve chamber in fluid communication with said proximal shuttle input port, said hydrophobic filter permitting substantially one-way ambient air flow to said entrainment valve chamber.

11. The percussive ventilation breathing head as claimed in claim 10 wherein said entrainment valve is removably attached said breathing head body.

12. A percussive ventilation breathing head adapted to be supplied with a flow of pulsatile gas and, independently, a flow of nebulized aerosol fluid comprising:
a breathing head body adapted to be supplied with the pulsatile gas flow at a proximal end of the breathing head, wherein said proximal end is close to a source of pulsatile gas flow supply, and said breathing head body defining an elongated interior passageway in said breathing head body;
a depending plenum carried by said breathing head body adapted to receive said nebulized gas flow;
an exhalation port;
a reciprocating injector shuttle movably mounted in said interior passageway, said shuttle adapted to move back and forth, distally and proximally, respectively due to said pulsatile gas and a bias acting on said shuttle, said shuttle having an internal flow passage from a proximal shuttle input port to a distal shuttle output port, said shuttle input port in fluid communication with said depending plenum, said shuttle input port being in fluid communication with said depending plenum such that nebulized aerosol gas from the depending plenum passes into the proximal shuttle input port, through the internal flow passage and through the distal end and the exhalation port of the elongated breathing head body under control of said shuttle; and
an entrainment valve on said breathing head body having a one-way gas flow system from ambient to an entrainment valve chamber in a top portion of said breathing head body, separate from the depending plenum, and in fluid communication with said proximal shuttle input port, wherein either
said one-way gas flow system includes a flapper valve biased closed and separating the ambient from said entrainment valve chamber such that said entrainment valve permits ambient air flow during an inhalation phase and the entrainment valve body having an over-pressure valve adapted to release aerosol to said ambient environment at a predetermined pressure, or
said one-way gas flow system includes a hydrophobic filter mounted in said entrainment valve body separating the ambient from said entrainment valve chamber and permitting substantially one-way ambient air flow to said entrainment valve chamber, such that said entrainment valve permits ambient air flow during an inhalation phase.

13. The percussive ventilation breathing head as claimed in claim 12 wherein said one-way gas flow system includes a flapper valve biased closed and separating the ambient from said entrainment valve chamber; and an over-pressure valve on said entrainment valve body adapted to release aerosol to said ambient at a predetermined pressure.

* * * * *